United States Patent [19]

Cardarelli

[11] 4,405,360

[45] Sep. 20, 1983

[54] CONTROLLED RELEASE OF HERBICIDE COMPOUNDS UTILIZING A THERMOPLASTIC MATRIX

[75] Inventor: Nathan F. Cardarelli, Barberton, Ohio

[73] Assignee: Environmental Chemicals, Inc., Wauconda, Ill.

[21] Appl. No.: 171,834

[22] Filed: Jul. 24, 1980

Related U.S. Application Data

[63] Continuation-in-part of Ser. No. 51,102, Jun. 22, 1979, Pat. No. 4,299,613, and Ser. No. 14,118, Feb. 22, 1979, Pat. No. 4,228,614, said Ser. No. 51,102, which is a continuation-in-part of Ser. No. 14,118, which is a continuation-in-part of Ser. No. 5,174, Jan. 22, 1979, Pat. No. 4,237,114, which is a continuation-in-part of Ser. No. 916,570, Jun. 19, 1978, Pat. No. 4,166,111.

[51] Int. Cl.$^3$ .............................................. A01N 37/38
[52] U.S. Cl. .......................................... 71/117; 71/65; 71/66; 71/67; 71/79; 71/86; 71/92; 71/93; 71/94; 71/105; 71/110; 71/116; 71/118; 71/120; 71/121; 71/DIG. 1; 521/92
[58] Field of Search ............... 71/DIG. 1, 66, 67, 117, 71/65, 79; 521/92

[56] References Cited

U.S. PATENT DOCUMENTS

| | | | |
|---|---|---|---|
| 3,062,634 | 11/1962 | Talbert | 71/66 |
| 3,062,760 | 11/1962 | Dermody et al. | 521/92 |
| 3,803,060 | 4/1974 | Roos et al. | 521/92 |
| 3,959,192 | 5/1976 | Delfosse et al. | 521/92 |
| 4,001,006 | 1/1977 | Nash | 71/117 |
| 4,012,221 | 3/1977 | Walker et al. | 71/66 |
| 4,015,970 | 4/1977 | Hennart | 71/DIG. 1 |
| 4,106,926 | 8/1978 | Thomas | 71/DIG. 1 |
| 4,244,728 | 1/1981 | Dellicolli et al. | 71/117 |
| 4,314,841 | 2/1982 | Scher | 71/DIG. 1 |

Primary Examiner—Glennon H. Hollrah
Attorney, Agent, or Firm—Lee, Smith & Jager

[57] ABSTRACT

A composition and method for the controlled release of compounds from a plastic dispenser, usually a thermoplastic, generally in association with a porosigen in contact with water, for example, an aquatic environment or soil mixture. Thermoplastic dispensers are generally made from a water insoluble polymer such as polyethylene, polypropylene, ethylene vinyl acetate, polyamide, polystyrene, polyvinyl acetate, polyurethane, etc. Thermoset plastics, such as epoxy, are also used. The porosigen, depending upon the desired end use and release rate of a compound, can have a solubility of less than 0.1 or 0.001 grams per 100 grams of water, or up to 100 grams per 100 grams of water. The released compound, for example, a herbicide, is contained in the thermoplastic dispenser. The combination of the plastic dispenser containing the porosigen and compound results in a slow release of a herbicide which can last for days, months, and even years, through dissolution of the porosigen and the formation of a porous network permitting water to contact the dispersed herbicide located in the interior portions of the dispenser.

10 Claims, 3 Drawing Figures

CONTROLLED RELEASE OF HERBICIDE COMPOUNDS UTILIZING A THERMOPLASTIC MATRIX

CROSS-REFERENCE

This application is a continuation-in-part of two of my copending applications, to-wit: "CONTROLLED RELEASE OF TRACE NUTRIENTS" filed June 22, 1979, bearing Ser. No. 51,102; now U.S. Pat. No. 4,299,613 and "FLOATING CHIP DISPENSER" filed Feb. 22, 1979, now U.S. Pat. No. 4,228,614, bearing Ser. No. 14,118. Application Ser. No. 51,102 is a continuation-in-part of application Ser. No. 14,118; which in turn is a continuation-in-part of my earlier copending application entitled "A METHOD AND COMPOSITION FOR THE LONG TERM CONTROLLED RELEASE OF A NON-PERSISTENT ORGANOTIN PESTICIDE FROM AN INERT MONOLITHIC THERMOPLASTIC DISPENSER" filed Jan. 22, 1979 as U.S. Ser. No. 5,174, now U.S. Pat. No. 4,237,114. Application Ser. No. 5,174 in turn is a continuation-in-part of an application bearing the immediately above title filed on June 19, 1978, as U.S. Ser. No. 916,570 now U.S. Pat. No. 4,166,111. A related application is entitled "CONTROLLED RELEASE OF COMPOUNDS UTILIZING A THERMOPLASTIC MATRIX" filed on July 24, 1980, bearing Ser. No. 171,835. now U.S. Pat. No. 4,400,374.

BACKGROUND ART

The present invention relates to the controlled release of herbicide compounds utilizing a plastic dispenser with a porosigen contained therein.

More specifically, the invention relates to the controlled release of herbicides for aquatic and terrestrial uses from a plastic dispenser.

It is well known that biocidal materials can be incorporated into an elastomer matrix and caused to release at a rate efficacious with pest destruction. U.S. Pat. No. 3,417,181 teaches that organotin toxicants can be dissolved in an elastomer-type matrix and caused to release through a diffusion-dissolution mechanism when exposed to water. The crux of this seminal invention was keyed to the necessity of the agent being soluble in the polymer. Similarly, U.S. Pat. Nos. 3,590,119; 3,426,473; 3,851,053; and 3,639,583 extend the scope of the art to embrace new formulations encompassing different elastomers, specific release regulants that affect the diffusion path length, and the like, but again the key concept is the necessity of agent solubility in the elastomer. Agents incorporated are organic pesticides, and the generic matrix type is elastomers such as natural rubber, styrene-butastyrene rubber, and the like. In contrast, U.S. Pat. No. 4,012,221 teaches that inorganic copper salts capable of being released into water are incorporated in a moderately crosslinked elastomer in which the copper salts are insoluble.

It is well known to the compounding art that agents not soluble within a polymeric matrix will not move at an efficacious rate through said matrix to said matrix surface and thus enter the ambient environment.

Almost all organic pesticidal agents lack solubility in plastic matrices whether thermoplastic or thermosetting. Similarly, inorganic pesticidal agents are likewise insoluble in known thermoplastic or thermosetting polymers. Similarly, inorganic chemicals utilized as trace nutrients in agriculture are insoluble in plastic materials.

One method of causing an insoluble organic agent to emit from a plastic dispensing unit is to use a third phase material that is (1) soluble in some extent in said plastic, and (2) will carry said organic agent in solution or serve as a migratory pathway for said agent to reach the surface of said dispenser. It is, of course, recognized that the incorporated agent must reach the plastic/external environment interface to have any effect on organisms inhibiting the external environment. U.S. Pat. Nos. 2,956,073 and 3,116,201 describe the use of plasticizers as carrier elements. In an improvement on such patents, U.S. Pat. Nos. 3,705,938 and 3,864,468 teach that surface loss from a plasticized matrix is subject to control through the use of a regulating membrane at said surface.

The controlled-release art has been generally confined to the incorporation and release of insecticides, bactericides, molluscicides and other toxic materials of an organic nature from an elastomer, wherein solubility is essential, or plasticized plastics, wherein an additive carrier material is critical. Microencapsulation processes, wherein an inner core of the toxic agent is surrounded by a polymeric matrix, is well known to the pest control art. In general, release is effected by the rupture of the enveloping membrane.

Little work has been hitherto performed in the development of efficacious long lasting fertilizing systems. U.S. Pat. No. 3,748,115 teaches that plant nutrients can be bound in a matrix of synthetic rubber, waxes, asphalt, and the like. In this work, four critical elements of the invention are set forth. The fertilizer, emphasizing bulk materials and not trace nutrients, must be uniformly dispersed in a hydrophobic binding element. The dispensing unit must be cylindrical in shape. Said cylinder must be partially coated with a water-insoluble, water-permeable exterior membrane. A portion of the cylinder must be non-coated with said membrane. U.S. Pat. No. 3,520,651 extends this art to teach that more than one nutrient can be incorporated in similar dispensing commodities.

Of course, fertilizing materials have long been compounded with various binders to facilitate dispersal and, in some cases, to prolong availability by slowing the rate of solution in water through precluding immediate nutrient element contact with water. U.S. Pat. No. 3,336,129 teaches that the use of small amounts of water insoluble copolymers and terpolymers of ethers, substituted ethers, ethylene oxide, and the like, will serve as carriers for fertilizing materials, said copolymers and terpolymers must be crosslinked. Materials are comprised of polymer+fertilizer+water+soil components and the plant is grown within this medium.

Also, fertilizers such as urea can be coated in a granular form as taught in U.S. Pat. No. 3,336,155, thus retarding solution in ground waters. U.S. Pat. No. 3,276,857 teaches that a fertilizer can be encapsulated with asphalt or various waxes and, thus, emission into the environment is slowed.

Other encapsulated patents include Japanese Pat. No. 4,428,457 wherein a granulated fertilizer leaches through a thin film; U.S. Pat. No. 3,059,379 wherein a fertilizer is encapsulated with the encapsulating film having holes or apertures therein; and U.S. Pat. No. 4,019,890 wherein granular fertilizers and coated with a water-resisting layer and forming a jelly-like gel coating thereon. U.S. Pat. No. 2,891,355 relates to coating shredded styrofoam with a solution of fertilizers and nutrients, adding water, and potting a plant therein. British Pat. No. 68,127 relates to utilizing very small amounts of a thermoplastic material as a binder to prevent bulk fertilizers such as urea, and other deliquescent nitrogen compounds from sticking together. Other patents in the area which do not relate to the present invention are Japanese Pat. No. 4,943,776 and U.S. Pat. Nos. 3,794,478; 2,791,496; 2,797,985; 3,372,019; and 4,111,684.

Turning to the area of larvicides, Boike et al has shown in examining 23 different organotin formulations and solute elastomer formulations that they were not effective under practical use conditions due to the presence of natural or organic substances common to water courses. Said organic materials rapidly absorb organotin molecules, essentially removing them from mosquito larva contact. In a text by Cardarelli, 1976, it was taught pesticides in an elastomer matrix can cause a slow-long duration release of the pesticide.

U.S. Pat. No. 4,012,347 relates to a rosin composition containing a film forming polymer, a solvent, and a pigment in which the rosin slowly flakes off, thereby exposing an organotin compound. U.S. Pat. No. 3,234,032 also relates to anti-fouling marine coating compositions wherein various organotin compounds are contained in waxes, oils, or paints. U.S. Pat. No. 3,236,739 relates to a bis(tributyltin)-adipate anti-fouling composition wherein the tin compound is dispersed in substantially water-insoluble film forming vehicles such as spar varnish, vinyl acetate-vinyl chloride copolymer paints, and the like.

In an article appearing in CHEMICAL ABSTRACTS, 75:97577c (1971), various non-organotin liquid pesticides are dispersed in various film-forming polymers, however, the system does not contain a porosigen or a water release system.

U.S. Pat. No. 4,010,141 relates to an organotin compound having a normal-dodecyl side chain such that the tin compound is soluble in and has bleedability from a thermoplastic. However, this patent fails to teach the use of a porosigen and actually teaches away from applicant's invention.

DISCLOSURE OF INVENTION

Accordingly, it is an object of the present invention to provide for the controlled release of herbicide compounds from a plastic dispenser.

It is yet another object of the present invention to provide for the controlled release of a herbicide compound from a dispenser, as above, comprising a thermoplastic or a thermosetting polymer as a binding matrix.

It is yet another object of the present invention to provide a dispenser, as above, containing a non-soluble thermoplastic or a thermoset plastic matrix.

It is yet another object of the present invention to provide for the controlled release of herbicide compounds from a thermoplastic dispenser, as above, wherein said thermoplastic includes polyethylene, low density polyethylene and high density polyethylene, ethylene-vinyl acetate copolymer, polypropylene, polystyrene, polyvinyl acetate, polyamide, polyester, polyurethane, and combinations thereof.

It is another object of the present invention to provide for the controlled release of herbicide compounds from a thermoset dispenser, as above, containing a thermoset such as phenolic, epoxy, amino resins, unsaturated polyesters, urethane foams, silicone polymers, and combinations thereof.

It is yet a further object of the present invention to provide for a controlled release aquatic herbicide in a plastic matrix, as above, wherein said herbicide destroys various undesirable aquatic plants.

It is yet another object of the present invention to provide a slow release terrestrial herbicide in a plastic matrix, as above, wherein said herbicide destroys various undesirable terrestrial plants.

It is a further object of the present invention to provide a controlled release plastic dispenser, as above, wherein a porosigen has a solubility in water of less than 0.1 or 0.001 grams per 100 grams of water but usually greater than 0.0005 grams per 100 grams of water.

It is still another object of the present invention to provide a controlled release plastic dispenser, as above, containing a porosigen having a solubility of from about 0.1 grams per 100 grams of water to about 100 grams per 100 grams of water.

It is yet a further object of the present invention to provide a controlled release plastic dispenser for releasing a herbicide in an aqueous environment, as above, wherein said dispenser floats.

It is yet another object of the present invention to provide a controlled release floating dispenser, as above, which may be in any of several forms, such as anchored strands, anchored chips, bimodal or polymodal pellets, and the like.

It is yet another object of the present invention to provide a floating dispenser, as above so shaped such that it is not covered during release over a period of months by various items such as silt, debris, and the like.

It is yet another object of the present invention to provide a floating thermoplastic dispenser, as above, wherein said floating dispenser may be attached to an anchor, as through a connecting member, for example, a line, or the like.

Another object of the present invention is to provide a controlled release plastic dispenser for releasing a herbicide in a terrestrial environment, wherein the dispenser is dispersed into the soil.

Still another object of the present invention is to provide a slow release plastic dispenser for releasing a herbicide in a terrestrial environment, as above, wherein a hygroscopic agent contained therein absorbs moisture to enhance release in less moist soil.

These and other objects of the present invention will become apparent from the following specification.

Generally, a controlled release herbicide dispenser, comprises: (a) from about 10 parts to about 160 parts by weight of a herbicide; (b) from about 1 part to about 80 parts by weight of a porosigen; and (c) about 100 parts of a polymer selected from the group consisting of thermoplastic polymers, thermoset polymers, and combinations thereof; said polymer in a matrix containing said herbicide and said porosigen to effect a controlled release of said herbicide, upon contact with water, to retard and eliminate growth of undesired plants.

Generally, a process for the controlled release of a herbicide from a dispenser, comprises: (a) adding and mixing 100 parts by weight of a polymer, from about 10 parts to about 160 parts by weight of a herbicide, and from about 1 part to about 80 parts by weight of a porosigen; (b) forming a matrix from said polymer within which said porosigen and said herbicide are dispersed; and (c) applying and contacting said matrix with the environment so that, upon contact with water, said herbicide will be released to retard and eliminate undesired plant growth.

BEST MODE FOR CARRYING OUT THE INVENTION

Figure 1:
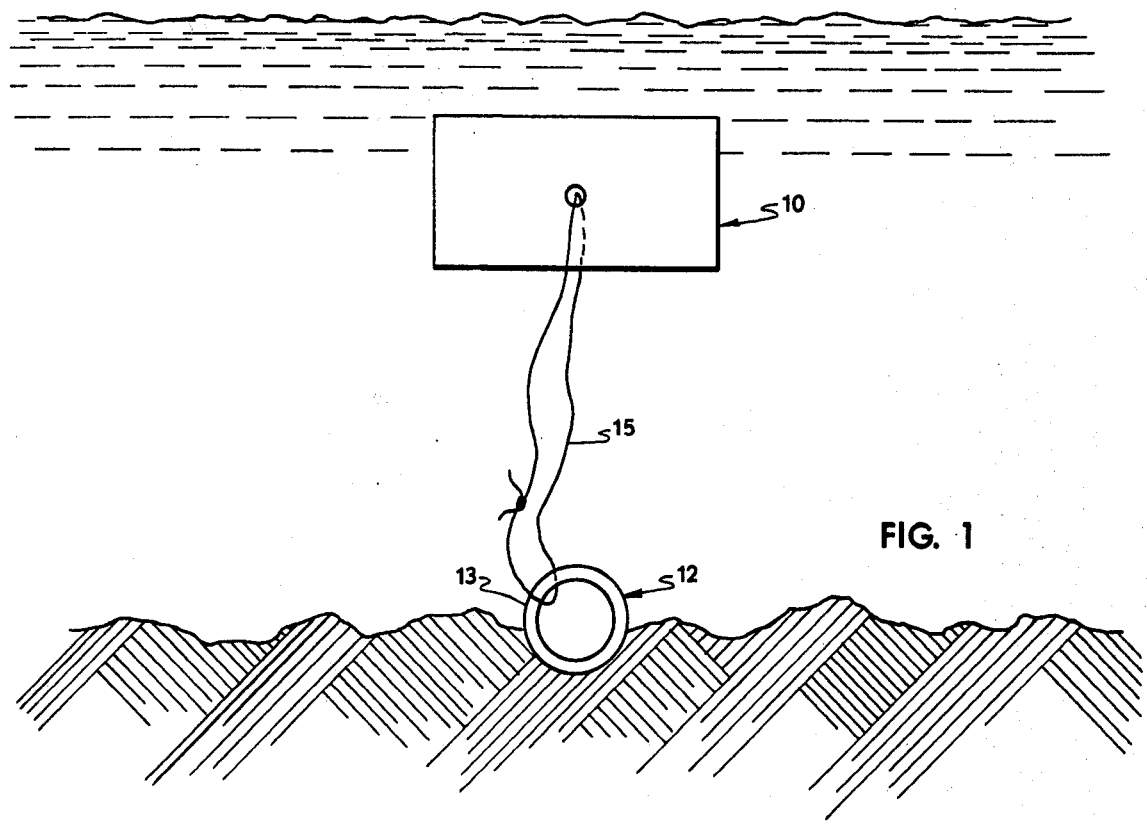
FIG. 1 is an elevational view showing a floating chip attached via a line to a weighted anchor which is resting on the bottom of a body of water.

The present invention relates to a sustained, controlled, or slow release of a herbicide compound from a thermoplastic dispenser or a thermoset dispenser also containing a porosity-enhancing compound, "porosigen" which, upon contact with water, either in an aquatic environment or a terrestrial environment, release of the said herbicide occurs.

In my prior copending continuing applications, my inventions relate to the sustained release of various pesticides, from a themoplastic matrix, or dispenser, against various aquatic pests such as insect larva, mollusks, and the like. Furthermore, my prior applications set forth the various specific pesticide compounds and the fact that the pesticide could be contained in a thermoplastic matrix which floated, that is, did not sink. Furthermore, my prior invention related to the use of a trace nutrient in the thermoplastic matrix so that upon contact with moisture, such as moisture from soil, the trace nutrient would be released and thereby stimulate plant growth. The exact nature of the various pesticides, various porosigens, as well as the trace nutrients contained within the thermoplastic matrix, as well as the concepts of the invention therein, are set forth in my previous continuing applications which are hereby fully incorporated by reference, especially with regard to all pertinent and essential matter. It is furthermore noted that all my previous continuing applications are incorporated by reference due to the length of the various specifications, but that various portions thereof will be set forth hereinbelow.

THERMOPLASTIC POLYMERS

Considering first the themoplastic polymers, that is polymers which soften and flow when heat and/or pressure is applied (the changes being reversible), they are well known to the art and are readily set forth in various references such as textbooks, journals, various encyclopedia, and the like, as for example, the various thermoplastics set forth in the MODERN PLASTICS ENCYCLOPEDIA, 1979-1980, Vol. 56, 10A, McGraw-Hill, as well as in other years, and the like, which are hereby fully incorporated by reference. Furthermore, the various properties thereof are well known as are the molecular weight distributions. For example, the number average molecular weight can range from about 10,000 to about 1,000,000, desirably from about 40,000 to about 500,000, and preferably from about 60,000 to about 250,000. Various thermoplastics can be utilized so long as a solid dispenser or plastic matrix is formed. However, it is noted that if a thermoplastic is soluble in water, it is not desired or a part of the present invention since the thermoplastic matrix dispenser will readily and rapidly degrade and not permit slow release over an extended period of time. Generally, thermoplastics which can be used include the various following thermoplastics, as well as common copolymers or terpolymers thereof. The various polyolefins containing from 2 to 10 carbon atoms. Specific examples include polyethylene, such as low density and high density polyethylene. Typically, low density polyethylene has a partially (approximately 50 to approximately 60 percent) crystalline solid structure, whereas high density polyethylene typically has over a 90 percent crystalline structure. Polypropylene can also be utilized. Additionally, various copolymers of ethylene may be utilized such as ethylene-propylene, and copolymers of ethylene and vinyl acetate.

An example of an ethylene-vinyl acetate copolymer includes those wherein the amount by weight of the ethylene units, based upon the total weight of the copolymer, ranges from about 60 percent to about 95 percent with a range of from about 80 percent to about 93 percent being preferred. The weight average molecular weight of the copolymer generally ranges from about 40,000 to about 400,000 and preferably from about 75,000 to about 300,000. Desirably, the copolymer has an ASTM Test #D1238 melt flow index of from about 6 to about 12 and preferably from about 7 to about 11 and a Vicat softening point of from about 70° C. to about 95° C. Since, apparently, the ethylene repeating units in the copolymer act as a regulator with regard to pore size, higher amounts of the ethylene constitutent will result in slower release times.

An example of an ethylene-propylene copolymer is those having a weight average molecular weight of from about 50,000 to about 250,000 with a preferred range of from about 100,000 to about 200,000. The percent by weight of the ethylene units can generally vary from about 30 percent to about 80 percent and preferably from about 45 percent to about 75 percent. The melt flow index of the ethylene-propylene copolymer can generally range from about 15 to about 45, and preferably from about 20 to about 32 according to ASTM Test #D1238 at 190°, 21600 gm,gm/10 minutes.

Moreover, in order to promote long release duration, it has been found useful, although not necessary, to blend the ethylene-vinyl acetate copolymer or the ethylene-propylene copolymer, or combinations thereof, with a polyethylene, especially low density polyethylene (that is, a density of from about 0.90 to 0.94 g/cc), having a melt flow index similar to said ethylene-vinyl acetate copolymer, that is from about 5 to about 14 and, preferably, from about 7 to about 11, and a weight average molecular weight of from about 100,000 to about 400,000. Thus, depending upon the rate of release, various amounts of low density polyethylene may be utilized. Generally, to obtain desirable release rates, the amount of homopolyethylene utilized may range from about 30 percent to about 75 percent and, preferably, from about 40 percent to about 60 percent by weight based upon the total weight of the blend of the ethylene-vinyl acetate copolymer, or the ethylene-propylene copolymer, or combinations thereof, and the polyethylene.

Polystyrene can be utilized as well as a family of styrene polymers which includes copolymers of styrene with other vinyl monomers or vinyl substituted aromatics having from 8 to 12 carbon atoms, polymers of derivatives of styrene, and the like. Thus, poly-alpha-methylstyrene may be utilized. Another group of thermoplastic polymers is the acrylic polymers with specific examples being polyacrylate, polymethylacrylate, and polymethylmethacrylate. The polyvinyl esters constitute yet another group with a specific example being polyvinylacetate. Still another group is the polyvinyl acetals such as polyvinylbutyral. The phenylene oxide-based thermoplastics can also be used. The various chlorine-containing polymers can be utilized such as polyvinylchloride, polytetrafluoroethylene, polychlorotrifluoroethylene, polyvinylfluoride, polyvinylidenefluoride, and the like. These polymers are used without plastication.

The polyamides or nylons are another group of thermoplastics and include Nylon 6, Nylon 10, Nylon 11, Nylon 12, Nylon 6,6, Nylon 6,10, and the like. Polyethers such as polyoxymethylene can be utilized. Another large group of thermoplastic compounds are the polyesters such as polyethylene terephthalate, polybutylene terephthalate, and the like. The polyurethanes constitute yet another group of thermoplastics. As known to those skilled in the art, the polyurethanes can be made from several types of polymers or prepolymers. The cellulose plastics are yet another group with specific examples being cellophane and rayon.

Desired thermoplastics include polyethylene, including low density polyethylene and high density polyethylene, copolymers of ethylenevinyl acetate, polypropylene, polybutene, polystyrene, poly-alpha-methyl styrene, polymethylmethalate, polymethylacrylate, polyacrylate, polymethylmethacrylate, polyvinyl acetate, polyvinyl butyral, polyvinyl chloride, polytetrafluoroethylene, polychlorotrifluoroethylene, polyvinyl fluoride, polyvinylidene fluoride, Nylon-6, Nylon-6,6, Nylon-6,10, polyoxymethylene, polyethyleneterephthalate, cellophane, rayon, and combinations thereof. Highly desired polymers include polyamide, polyvinyl acetate, polyurethane, and combinations thereof.

Preferred thermoplastics include polyethylene (including low or high density polyethylene), a copolymer of ethylene-vinyl acetate, polystyrene, polypropylene, polyester, and alloys thereof.

THERMOSET POLYMERS

The various plastic compounds generally referred to as thermoset compounds can also be utilized.

Thermoset compounds are generally defined as those which change irreversibly under the influence of heat from a fusible and soluble material into one which is infusible and insoluble through the formation of a covalent crosslinked, thermally stable network, or without heat through the addition of a highly chemically active crosslinking agent. The thermoset compounds or resins are furthermore those in which crosslinking occurs simultaneously with the final steps of polymerization, regardless of the amount of heat required in this step. Thus, the thermoset, the porosigen, and the compound to be slowly released are thoroughly mixed or dispersed and then heated, whereupon a thermoset matrix is formed, or said highly active chemical crosslinking agent added. The matrix, if need be, is then reduced to an appropriate size through any conventional method, e.g., a pelletizer, whereupon a suitable dispenser is formed.

Thermoset compounds are well known to those skilled in the art and are set forth in various texts, encyclopedias, journals, etc., such as the MODERN PLASTICS ENCYCLOPEDIA, 1979-1980, Vol. 56, No. 10A, McGraw-Hill, which is hereby fully incorporated by reference. Examples of thermoset compounds include the various phenolic resins, the various amino resins such as melamine and the like. The unsaturated polyester resins may also be utilized as can the various epoxy resins. Still further, the various urethane foams which are crosslinked may be utilized as can the silicone polymers. Also, the various thermoset polyimides can be used. Generally, specific thermosets which can be used include conventional and known compounds, such as those set forth in various texts, encyclopedias, and the like.

Naturally, any of the above thermoplastics and thermosets may be utilized including combinations thereof. It is generally desirable to use the low cost compounds. Of the thermosets, the various phenolics and the various epoxies are preferred.

TRACE NUTRIENT COMPOUNDS

The various trace elements utilized as nutrients are generally in the form of salts or oxides, which are readily available, desirably low in cost, and are not highly deliquescent. It is noted that the term "salts" includes the various hydrates thereof, that is the mono-, and di-, the tri-, the tetra-, the penta-, the hexa-, the hepta-, etc. Should the salt not exist in the non-hydrate form, the most common forms are meant. With regard to zinc-containing compounds which may be utilized as trace nutrients, they include the following: zinc sulfate, zinc chloride, zinc carbonate, zinc oxide, zinc phosphate, zinc chlorate, zinc nitrate, the various existing hydrates thereof, and the like. Typical copper trace nutrient compounds include copper sulfate, copper carbonate, copper oxide, copper oxychloride, copper nitrate, copper phosphate; various copper complexes such as tetraamines, diamines; the various existing hydrates thereof, and the like. Typical iron trace nutrient compounds include iron chloride, iron sulfate, iron oxide, the various existing hydrates thereof, and the like. Typical manganese trace nutrient compounds include manganese oxide, manganese sulfate, manganese chloride, manganese nitrate; the various existing hydrates thereof, and the like. Typical boron trace nutrient compounds include boric acid, sodium biborate; and various hydrates thereof, and the like. Typical molybdenum trace nutrient compounds include molybdenum oxide, sodium molybdate, potassium molybdate, the various existing hydrates thereof, and the like. Typical cobalt trace nutrient compounds include cobalt sulfate, cobalt chloride, cobalt nitrate; the various existing hydrates thereof, and the like. Typical selenium trace nutrient compounds include sodium selenate, selenium dioxide, selenium trioxide, selenium disulfide, selenium sulfur oxide, and the like. Typical magnesium compounds include magnesium carbonate, magnesium sulfate, magnesium nitrate, magnesium acetate, magnesium oxide, magnesium chloride, magnesium ammonium chloride, magnesium phosphate, magnesium sulfite, the various existing hydrates thereof, and the like. Typical chromium compounds include chromium (II) sulfate, chromium chloride, chloropentammine chromium chloride, the various hydrates thereof, and the like.

Desirably, the amount of trace nutrient released by the polymer dispenser is such to make a plant grow, to stimulate plant or animal growth, and to supplement the environment. Thus, exact amount will vary from site to site, soil to soil, crop to crop, animal to animal, and the like. As approximate rule of thumb, the dispenser or mixture can contain from about 1 percent to about 60 percent by weight of a particular trace nutrient ion based upon the total weight of the dispenser, pellet, etc. From about 2 to about 50 percent is desirable, with from about 4 to about 40 percent being more desirable. The amount of trace nutrient generally ranges from about 10 to about 160 parts by weight based upon 100 parts by weight of the polymer, desirably from about 25 to about 125, and preferably from 50 to about 100 parts by weight. Naturally, more than one trace nutrient may be utilized in the dispenser and thus several may be utilized. Furthermore, since some of the trace nutrients serve as a porosity agent itself, it is not always necessary to utilize a porosigen, although a porosigen is generally preferred, and will hasten the release rate. Trace nutrients, which have a fair degree of solubility, include zinc sulfate, zinc chloride, copper sulfate, copper oxychloride, iron sulfate, iron chloride, manganese sulfate, manganese chloride, boric acid, sodium biborate, sodium molybdate, cobalt sulfate, and sodium selenate.

Controlled release trace nutrients are usually added directly to the soil by conventional application means. Selection is based upon need as well as the particular nature of the soil. For example in alkaline soil needing iron, a choice selection would be an iron salt soluble in the alkaline range, whereas in acid soil, the selection would be a salt soluble in the acid pH range. Also, additives such as lime might be similarly added to the matrix in order to change the soil pH in the immediate vicinity of the dispenser in order to induce more rapid trace nutrient release and plant absorption.

Controlled release trace nutrients are not only of value to crop production, but also to pasturage, forestry, horticulture, and the like, and such uses are hereby implied.

Controlled release trace nutrients may also be added directly to livestock production, such as beef cattle, poultry, sheep, sevine, and the like, as an additive to feed.

PESTICIDE COMPOUNDS

Pesticides are pesticide compounds which kill things undesirable to man, for example, animals, such as insects, and the like. Various pesticides are effective against aquatic pests such as mosquito larva, black fly larva, midge larva, the molluscan hosts of trematode parasites, for example, snails, and some cases the aquatic larva forms of such parasites, and the like. Examples of pesticides which are effective against aquatic animal pests include tetramethyl-O,O'-thiodi-p-phenylene phosphorothioate (commonly referred to as Temephos), an organotin compound having the formula $R_3S_nX$, wherein $R_3$ is an alkyl group having from 1 to 8 carbon atoms, desirably from 3 to 6 carbon atoms, and preferably 3 carbon atoms, that is, propyl and the isomers thereof being preferred. An alkyl group having 4 carbon atoms, that is butyl, and the various isomers thereof is highly preferred. Additionally, the organo portion R of the tin toxicant may be an aryl group or a substituted aryl group with the substituted portion being an alkyl or an ester group containing from 1 to 6 carbon atoms. Specific examples of such compounds include phenyl, phenyl acetate, phenyl propionate, phenyl isobutyrate, and the like.

The anion or "X" portion of the organotin compound can be a halogen, an oxide, an alkoxy $OR^1$, wherein $R^1$ is an alkyl and contains from 1 to 12 carbon atoms, or an

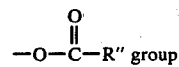

where $R''$ is an alkyl having from 1 to 12 carbon atoms, such as propionate, butyrate, pentyate, hexylate, and the like, with acetate being preferred. Of the various anions, the halogens are preferred with fluorine being highly preferred. Thus, tributyltin fluoride is preferred, with tributyltin acetate, triphenyltin fluoride, tributyltin oxide, and triphenyltin acetate being desired compounds.

Another effective pesticide is 2-(1-methylethoxy)-phenol methylcarbamate, commonly known as Baygon, manufactured by Mobay Chemical Company of Kansas, Mo., O,O-diethyl-O-(3,5,6-trichloro-2-pyridyl)phosphorothioate, commonly known as Dursban; and the O,O-dimethyl phosphorodithioate ester of diethyl mercaptosuccinate, commonly known as Malathion. These compounds, along with Temephos, Dibrom and Fenitrothion are preferred. Other examples include Dibrom or Naled (dimethyl-1,2-dibromo-2,2-dichloroethyl phosphate; Thiodan, i.e., 6,7,8,9,10,10a-hexachloro-1,5,5a,6,9,9a-hexahydro-6,9-methano-2,4,3-benzodioxathiepen-3-oxide; Lindane, that is Gamma-1,2,3,4,5,6-hexachlorocyclohexane; Sevin, that is 1-naphthyl methylcarbamate; Propoxur, that is, 2-(1-methylethoxy)-phenol methylcarbamate; Rotenon, that is, 1,2,12,12a-tetrahydro-2-isopropenyl-8,9-dimethoxy-(1)-benzopyrano-(3,4,6)-furo-(2,3,6) (1)-benzopyran-6(6aH) one; DDT, that is, dichlorodiphenyltrichloethane; Methoxychlor, that is, 2,2-bis(p-methoxyphenyl)-1,1,1-trichloroethane; Dimilin, that is, N-[(4-chlorophenyl)-(amino)(carbonyl)]-2,6-difluorobenzamide; Dichlorvos, that is, dimethyl 2,2dichlorovinyl phosphate; Fenitrothion, that is, O,O-dimethyl-O-(3-methyl-4-nitrophenyl)-phosphorothioate; Fenthion, that is, O,O-dimethyl-O-[3-methyl-4-(methylthio)(phenyl)] phosphorothioate; Dimethoate; that is, O,O-dimethyl-S-(N-methylcarbomoyl methyl)phosphorodithioate; Methidathion (Suprocide), that is, O,O-dimethyl phosphorodithioate, S-ester with 4-(mercaptomethyl)-2-methoxy-1,3,4-thiodiazoline 5-one; and, Temephos, that is, O,O,O,'O'-tetramethyl-O-thiodi-p-phenylene phosphorothioate.

Based upon 100 parts of the polymer dispenser, that is the thermoplastic or the thermosetting compound, the amount of the aquatic pesticide ranges from about 2 parts to about 70 or 80 parts by weight, desirably from about 3 parts to about 50 parts, and preferably from about 5 parts to about 20 parts by weight. However, when the aquatic pesticide is an organotin compound, the amount is from about 25 to about 75 parts with from about 40 to about 70 parts being preferred.

POROSIGEN

The type of porosigen can vary depending upon the desired release rate sought. Thus, a porosigen having a moderate or low solubility can be utilized, that is a solubility of approximately 0.1 grams or less per 100 grams of water with a solubility of approximately 0.01 grams or less per 100 grams of water often being desired. The lower limit of solubility is generally that which will give a suitable release rate for a specific application. Such a release rate will vary depending upon the amount of porosigen, the amount and type of herbicide compound, the amount of dispenser utilized, and the like, all of which can be readily determined by one skilled in the art. Thus, porosigens can be utilized which are very slightly soluble or barely soluble. Generally, a lower solubility limit of about 0.0005 grams per 100 grams of water is desired.

Additionally, a porosigen may be utilized which has a higher solubility of between 0.1 to about 1 gram per 100 grams of water, or from about 1.0 gram, or about 10 grams to about 100 grams per 100 grams of water. That is, a porosigen may be utilized having a solubility in the range of from about 0.1 to about 100 grams per 100 grams of water, or a sub-range thereof.

The porosigen, regardless of solubility, may generally be any compound which is inert with regard to the types of polymer, the herbicide, the trace nutrient, the aquatic larvicide, etc., incorporated therein. That is, by inert, it is meant that the porosigen does not chemically react with the polymer, herbicide, or other active agent, trace nutrient, pesticide compound, etc., or otherwise render the dispenser ineffective for its intended purpose. Furthermore, it should not be damaging or harmful to the environment in terms of toxicity. The porosigen can generally be any compound which is set forth in the Handbook of Chemistry and Physics, 1977-78, published by the Chemical Rubber Company, which is hereby fully incorporated by reference, which meets the above requirements with regard to solubility, inertness, and being non-harmful to the environment.

With regard to the low or moderate solubility porosigens, a suitable porosigen includes the inorganic salts or the hydrates thereof, or oxides. The cation of such a salt may generally be any of the alkaline metals and preferably any of the non-toxic alkali or alkaline earth metals, Column 1A and 2A, respectively, of the Periodic Table. Additionally, various other metals may be utilized such as iron, nickel, zinc, tin, silver, and the like. The anion portion of the salt may generally be any negative charge entity, as the various carbonates, the various bicarbonates, the various nitrates, nitrites, or nitrides, the various sulfates, sulfites, or sulfides, the various phosphates, phosphites, or phosphides, including the ortho-, pyro-, hypo-, variations thereof, and the like. Generally, the sulfates, sulfites, and sulfides are preferred as anions, with carbonates being highly preferred. Moreover, as noted above, the anion may be an oxide of the metal. Specific examples of porosigens include magnesium carbonate, magnesium sulfide, magnesium phosphide, magnesium oxide, calcium carbonate, calcium bicarbonate, calcium nitride, calcium oxide, calcium phosphate, calcium phosphite, calcium sulfide, calcium sulfite, iron carbonate, iron sulfate, iron sulfide, iron sulfite, nickel carbonate, nickel sulfide, zinc carbonate, zinc sulfide, zinc sulfite, tin sulfide, tin oxide, silver carbonate, silver oxide, silver sulfide, silver sulfite, sodium bicarbonate, lithium phosphate, beryllium oxide, strontium carbonate, strontium sulfate, and strontium sulfite. Magnesium carbonate and strontium carbonate ar preferred, with calcium carbonate being highly preferred.

With regard to the higher solubility porosigens, the inorganic salts, or hydrates or oxides thereof, of the alkali metals and the alkaline earth metals, Column 1A and 2A, respectively, of the Periodic Table, as well as of nickel, iron, zinc, tin, and silver, which have a solubility of at least 0.1 grams/100 grams of water and up to about 100 grams per 100 grams of water can be utilized. Desirably, the halogen or carbonate salts of these cations, having a solubility of at least 0.1 grams/100 grams of water and up to about 100 grams/100 grams of water, can be used. Of the halogen salts, the chloride salts are preferred. The Handbook of Chemistry and Physics, 1977-78 Edition, Supra. is hereby fully incorporated as to such specific compounds since the list is rather extensive. Additionally, ammonia as a cation constitutes another class of salts with specific examples being ammonium bromide, ammonium carbonate, ammonium bicarbonate, ammonium chlorate, ammonium chloride, ammonium fluoride, ammonium sulfate, and the like. Of these higher solubility porosigens, sodium bicarbonate, sodium carbonate, and ammonium sulfate are preferred.

For the amount of porosigen when utilized with the trace nutrients and pesticides, the range is from 0.1 to about 70 parts by weight based upon parts of the polymer, although up to 100 parts may at times be utilized. If a porosigen is utilized having a solubility of greater than 0.1, that is from about 0.1 to about 100 grams per 100 grams of water, the amount desirably ranges from about 1 to about 30 parts and preferably from about 2 to about 12 parts. If a porosigen has a solubility of less than 0.1 parts or less than 0.01 parts per 100 parts of water, that is down to about 0.0005 grams per 100 grams of polymer, the desired amount ranges from about 5 to about 70 with a preferred amount ranging from about 15 to about 35 parts per 100 parts of the polymer. The porosigens having a porosity of from about 0.1 to about 100 grams per 100 grams of water are generally preferred so that a quicker release of the trace nutrient is obtained.

With regard to the pesticides, the amount of porosigen is as previously set forth; that is, if the porosigen has a solubility of 0.1 or less, for example, to about 0.0005 grams per 100 grams of polymer, the range is from about 5 parts to about 70 parts by weight of desirably from about 15 to about 35 parts per 100 parts of polymer. If a porosigen having a solubility of 0.1 or greater is utilized, the amount of porosigen ranges from about 1 part to about 60 parts, with 2 parts to about 20 parts being desired.

OTHER DISPENSER CONSTITUENTS

The composition, in addition to the above mentioned compounds, can contain conventional additives to enhance dispersion, add color, aid in processing, or to alter density. Thus, from about 0.2 to about 10 or 20 parts by weight of an insoluble compound such as zinc stearate per 100 parts by weight of the polymer may be utilized as a dispersant. Usually, an amount up to about 5 or 10 parts, and even up to 1 or 2 parts is often used.

The ability of the herbicide, pesticide, or trace nutrient to leave the dispensing unit and pass into the ambient environment wherein dwells the target organism is dependent upon contact with moisture. This moisture can penetrate the dispenser via movement through a pore structure into said dispenser wherein said herbicide, pesticide, or trace nutrient can be solvated by ingressing moisture and thus move outward through diffusion. Such a system is termed leaching.

In order to create said porosity and thus allow leaching to occur, the porosigen additive must first be solvated and removed as described above. However, in some cases, the herbicide, the pesticide, or the trace nutrient molecule may be of too great a physical size to move conveniently from the occupied spaces, or intermolecular voids, between matrix molecules. This volume, termed herein as "free volume," can at times play a critical role in release of the incorporated agent into the growing pore network. It has been discovered that free volume can be altered through the specific incorporation of a secondary polymer. Where agent molecule dimensions are large, an increase in free volume improves the rate of agent movement from the interstitial spaces into the water-filled pore. In order to increase free volume and thus improve efficacy, a secondary polymer at melt index, widely variable from the binding, or matrix, polymer is utilized. The thermoplastic or thermoset polymers previously discussed are available at a variety of melt indices. Selection of the second polymer is predicated on the melt index of that polymer with the melt index of the primary polymer used to create the matrix. For example, if the matrix polymer has a melt index of 1.5, the secondary polymer has a melt index of 1.5, the secondary polymer selected would have a melt index of 6.0 or greater, a disparity of 5 to 25 melt index units being desirable. For example, when low density polyethylene is the desired polymer, a free volume is activated by use of ethylene-propylene copolymer therewith, because of the difference of melt indices of these two compounds.

HERBICIDE COMPOUNDS

A herbicide is a chemical substance used to destroy plants. Plants undesirable to man or his environment may be destroyed by the herbicides of the present invention. Herbicides in the composition of the present invention are released at a controlled rate to sustain obstruction of undesirable plant growth over long periods of time. The controlled release herbicide activity is desired for borth aquatic and terrestrial environments.

Herbicides to be used in the composition of the present invention depend upon the plant desired to be destroyed. Therefore, the class of herbicides known to those skilled in the art of destroying undesirable plants are compounds within the concepts of the present invention. Representative examples of herbicides known to those skilled in the art are the following available chemicals, expressed in common name and chemical nomenclature in parentheses: Alachlor (Lasso), 2-chloro-2',-6'-diethyl-N-(methoxymethyl)acetanilide; Treflan (Trifluralin), $\alpha,\alpha,\alpha$,trifluoro-2,6-dinitro-N,N-dipropyl-p-toluidine; Propachlor (Ramrod) 2-chloro-N-isopropylacetanilide; Basagran (Bentazon) 3-isopropyl-1H-2,1,3-benzothiadiazin-(4) 3H-one-2,2-dioxide; Metribuzin (Lexone) 4-amino-6-(1,1-dimethylethyl)-3-(methylthio)-1,2,4-triazin-5-(4H)-one; Dicamba (Banvel), 3,6dichloro-O-anisic acid; Glyphosate (Round Up), N-(phosphonomethyl)glycine isopropylamine salt of Sutan S-ethyl diisobutylthiocarbamate; Butralin (Amex 820) [4-(1,1-dimethylethyl)-N-(1-methylpropyl)]-2,6-dinitrobenzenamine; Carbyne (Barban) 4-chloro-2-butynyl-m-chlorocarbanilate; Avadex, S-2,3-dichloroallyl diisopropylthiocarbamate; Eptam (EPTC), S-ethyl dipropylthiocarbamate; Lorox (Linuron) 3-(3,4-dichlorophenyl)-1-methoxyl-1-methylurea; Paraquat (Gramoxono), 1:1-dimethyl-4,4'-bipyridinium(cation)dichloride; Amiben (Chloramben), 3-amino-2,5-dichlorobenzoic acid; Cotoran (Zanex) (Fluometuron), 1,1-dimethyl-3-(2,a,a-trifluoro-m-tolyl) urea; Karmex (Diuron), 3-(3,4-dichlorophenyl)-1,1-dimethylurea; Krenite, ammonium ethyl carbamoylphosphonate; Pronamide (Kerb), 3,5-dichloro-N-(1,1-dimethyl-2-propyl)-benzamide; Picloram, 4,amino-3,5,6-trichloropicolinic acid; Penoxalin (Prowl), N-(1-ethylpropyl)3,4-dimethyl-2,6-dinitro benzenamine; Propanil (Stam), 3,4-dichloropropionanalide; Atrazine, 2-chloro-4-ethylamino-6-isopropylamino-S-triazine; 2,4-D acid, 2,4-dichlorophenoxy acetic acid; Fenac, 2,3,6-trichlorophenylacetic acid; Bromacil, 5-bromo-3-sec.-butyl-6-methyluracil; Simazine (Princep), 2-chloro-4,6-bis(ethylamino)-S-triazine; Diquat, 6,7-dihydrodipyrido(1,2a'2'1'-c)pyrazidiinium dibromide; Dichlobenil (Casoron), 2,6-dichlorobenzonitrile; Dacthal, dimethyl tetrachloroterephthalate; Machete (Butachlor), 2-chloro-2,6-diethyl-N-(butoxymethyl)acetanilide; Surflan, 3,5-dinitro-N,N-dipropylsulfanilamide; Tolban (Profluralin), N(cyclopropylmethyl)-$\alpha,\alpha,\alpha$-trifluoro-2-dinitro-N-propyl-p-toluidine; 2,4-D amine (Decamine), dimethylamine salt of 2,4-dichlorophenoxyacetic acid; 2,4-D ester (Weedone LV-4), isooctyl ester of 2,4-dichlorophenoxy acetic acid.

Of these herbicides, the following are desired: Alachlor, Treflan, Dicamba, Glyphosate, Diuron, Carbyne, Pronamide, Penoxalin, 2,4-D acid, Fenac, Bromacil, Atrazine, Simazine, Diquat, Dichlobenil, 2,4-D amine, 2,4-D isooctyl ester, and the butoxyethanol ester.

Of these herbicides, the following are preferred: Treflan, Glyphosate, Diuron, Pronamide, Fenac, Bromacil, Diquat, Alachlor, Dichlobenil, 2,4-D amine and 2,4-D isooctyl ester.

These herbicides function to destroy a variety of undesirable plants, even in the presence of crops for human or animal consumption. For example, the following table indicates herbicides representative of the list above and the crops they protect.

TABLE 1

| | Agent, Usage and Manufacturers | | |
|---|---|---|---|
| Agent | Manufacturers | Type | Crops |
| Diruon | DuPont et al | Pre- & Post-Emergence | Cotton, fruits, nuts, oats, sugar cane, wheat, citrus, alfalfa, sorghum (also non crop areas) |
| Simazine | Ciga-Geiby | Pre-emergence | Alfalfa, orchards, citrus, corn, grapes, grasses (sod), nuts, sugar, olives |
| Diquat | ICI(Chevron-U.S.) | Pre-harvest dessicant | Cotton, potato, clover, soy beans, sugar cane |
| Fenac | Tenneco, Amchem | — | Non-crop areas |
| | | Pre-emergence | Sugar cane |
| Bromacil | DuPont | — | Non-crop areas |
| | | Pre-emergence | Sugar cane |
| Atrazine | Ciga-Geigy | Pre & post-emergence | Corn, pasture, sugar cane, sorghum, forest, turf grass |
| Dichlobenil | Thompson-Hayward | — | Nuts, fruits, berries, alfalfa, ornamentals |
| 2,4-D acid + ester + amine | Thompson-Hayward Rhodia, Amchem, Dow etc. | Post-emergence | Fruits, grains, grass, rice pastures, sorghum, wheat, sugar cane |
| Treflan | Elanco | Pre-emergence | alfalfa, cabbage, carrots, celery |

TABLE 1-continued

| Agent | Manufacturers | Type | Crops |
|---|---|---|---|
| Glyphosate | Monsanto | Post-emergence | citrus, cherries, corn, beans, nuts sugar, wheat small grains, corn, soybeans, orchards, vineyards, rubber, palms, coconut, cocoa, coffee, tea, bananas |
| Pronamide | Rohm & Haas | Pre-emergence early post-emergence | alfalfa, lettuce, clover, turf |
| Alachlor | Monsanto Co. | Pre-emergence | soy beans, corn, cotton, potatoes, and peanuts |

Herbicides are needed for destruction of undesired plants in both the aquatic and terrestrial environments. Again, the herbicides to be used may be adaptable to aquatic or terrestrial environments according to the chemical activity of the herbicide. This information is known or readily discernible to a person skilled in the art. For example, all of the herbicides listed above can be terrestrial herbicides and the following herbicides can be used as well in aquatic environments. Diuron; Simazine; Diquat; Fenac; Bromacil; Atrazine; Dichlobenil; 2,4-D acid; 2,4-D amine; and 2,4-D isooctyl ester.

In the concentration of the herbicide or combinations of herbicides in the controlled release compound of the present invention can range from about 10 parts to about 160 parts by weight per 100 parts of polymer. Desirably, the concentration of the herbicide or herbicides may range from about 15 parts to about 100 parts by weight per 100 parts of polymer. Preferably, the concentration of the herbicide or herbicides may range from about 20 parts to about 50 parts by weight per 100 parts of polymer. With any of these concentrations, it is remembered that the rate of dispersal of herbicide, its effective concentration at a given point in time, is dependent upon the concentration of the porosigen and the porosity rate. Therefore, these concentration ranges represent the total potential concentration of herbicide over the duration of controlled release.

The concentration of the porosigens described above for use in the controlled release composition having herbicides ranges from about 1 part to about 70 or 80 parts by weight per 100 parts of polymer. This concentration is applicable to the low or moderate solubility porosigens and the higher solubility porosigens.

For the low or moderate solubility porosigens, it is desired to have a concentration from about 5 parts to about 70 or 80 parts by weight per 100 parts of polymer. Preferably, this porosigen group ranges in concentration from about 15 to about 35 parts by weight per 100 parts of polymer.

For the higher solubility porosigens, it is desired to have a concentration from about 1 to about 40 parts by weight per 100 parts of polymer. Preferably, this porosigen group ranges in concentration from about 1 part to about 30 parts by weight per 100 parts of polymer. Optimally, the range of porosigen concentration varies from about 12 parts to about 25 parts by weight per 100 parts of polymer.

POROSIGEN MODIFYING AGENTS

In addition to the porosigens of the present invention, the controlled release composition may contain porosity modifying constitutents. These constituents may be combined with the porosigens to provide a multi-stage creation of the pore structure, hydroscopic attraction, inducement activation, or inhibition of porosity or other complementary features. For example, inert liquids compatible with and dispersible in the polymer such as lower aliphatic and glycerol glycols may be utilized. The glycols, which are highly water soluble, often will activate the porosigen by permitting more rapid water ingress and thus faster contact between a porosity, such as $CaCO_3$ or $(NH_4)_2SO_4$, and water. Of these glycols, ethylene glycol is preferred. These glycols may be added in an amount from about 2 parts to about 6 parts by weight per 100 parts of polymer.

Another porosity constituent is soy oil, or other organic compounds similar in properties. Soy oil is preferred, because it tends to be water insoluble and thus blocks or inhibits pore formation. This constituent may be added in an amount from about 2 parts to about 25 parts and desirably from about 2 parts to about 6 parts by weight per 100 parts of polymer.

Another porosity constituent is silicon dioxide. This constituent, which is nearly water insoluble, can be used to inhibit or slow down the growth of a pore network arising from the loss of a porosigen by water contact and solvation. This constituent may be added in an amount from about 2 parts to about 25 parts by weight per 100 parts of polymer. These other porosity constituents are not necessary for the creation of the controlled release compositions, but they may be added in various combinations or individually to complement the functions of the porosigens, and control porosity rate to suit particular terrestrial or aquatic conditions.

MECHANISM OF CONTROLLED RELEASE

According to the concepts of the present invention, the controlled release of a compound such as a herbicide, is released from the thermoplastic or thermoset dispenser over a period of time. The mechanism of release depends upon exposure of the porosigen to moisture or water, that is with the dispenser actually residing within a body of water or residing on or in the soil and therefor subject to soil moisture. When contained in the soil, the dispenser is in integral contact therewith, and the compound is released directly into the soil.

Since the porosigen is thoroughly mixed, blended, or dispersed throughout the dispenser along with the compound, various portions of the surface of the dispenser will contain portions of porosigen. Thus, upon contact with soil moisture or water, the porosigen will slowly dissolve and, in this process, create a porous network or structure through the thermoset or thermoplastic matrix of the dispenser. This process permits the water to contact the now-exposed herbicide compound, the herbicide dislodges from the matrix and is actually released; that is, actually drawn out of or removed from the dispenser. This dissolution process of the porosigen results in the gradual and controlled release of the herbidide compound in the water or soil moisture over a period of time such as from a period of weeks, months, or even years.

The herbicide compounds to be released are generally insoluble to the polymer. Since they are thoroughly mixed or dispersed throughout the dispenser with the polymer matrix, they will not be released in any significant amounts with regard to efficacy, if they are released at all. However, the dispersement or mixture of the porosigen in the polymer matrix provides a suitable controlled release mechanism. Moreover, should a particular compound be soluble and/or a liquid, it is still generally slowly released in a controlled manner, since it is dispersed throughout the matrix and generally is not released except through the pore structure created by the porosigen.

PREPARATION OF CONTROLLED RELEASE COMPOSITION

The slow or controlled release dispenser is prepared by mixing, blending, etc., the herbicide compound, and others, such as the trace nutrient and the pesticide, with the thermoplastic polymer and the porosigen in suitable proportions as indicated herein in any conventional mixing apparatus along with various additives such as colorants, dispersants, and the like. The mixture is coalesced by generally heating it above the softening point and preferably above the melting point of the thermoplastic polymer. The result is a slow release dispenser having a polymer matrix, wherein the herbicide is thoroughly mixed or dispersed. Dispersion is preferred to be monolithic; that is, the compound usually exists as an individual entity or site, throughout the dispenser. Naturally, the porosigen is also mixed or dispersed throughout the dispenser. The dispenser may be made into any manner, shape, or form. Thus, if the compounds are mixed and extruded from an extruder, they may be in the form of ribbons, or chopped into pellets, chips, or the like. Naturally, the temperature of the coalescing apparatus relates to the softening or melting point of the thermoplastic polymer and may range from about 170° C. to about 190° C., or from about 120° C. to about 220° C., although lower or higher temperatures may be utilized depending upon the thermoplastic. Additionally, the dispenser can be prepared by melt casting, solution casting, and the like, such techniques known to the plastic processing art.

Similarly, when a thermoset plastic is utilized, the herbicide, the trace nutrient, or the pesticide, the thermoset plastic, and the porosigen are mixed, blended, etc., at a temperature below the polymerization temperature of the thermoset. The mixing or blending desirably creates a monolithic dispersion. Then, the mixture is heated in an extruder or other conventional apparatus to produce the dispenser in any suitable size, shape, etc. Should the size not be suitable, etc., the matrix can be cut, chopped, etc., by conventional apparatus to achieve a suitable size, etc.

AQUATIC DISPENSER METHODS

For aquatic herbicidal activity, the dispenser of the present invention with regard to the aquatic pesticide may be applied to any aquatic environment such as ponds, lakes, rivers, streams, swamps, waterways, and the like.

However, such bodies of water will often fill up with silt, debris, and the like, thereby covering the dispenser, as in the form of a pellet, granule, or the like, and thereby adversely affecting release. On the other hand, it can be washed away. Thus, it is often desirable to incorporate the thermoplastic or thermosetting dispenser in a floating form connected to an anchor. In such a manner, the dispenser will reside above the bottom of an aquatic body of water and effectively operate for the entire life of the dispenser.

The floating dispenser should have a density of less than 1.0 grams per cc, that is a specific gravity less than 1.0. The density can be controlled through proper selection of components including polymers, that is, thermoplastics or thermoset, lightweight fillers, as well as the use of common and conventional blowing agents known to those skilled in the art. Often, the density of the dispenser will be less than 1.0 grams per cc and thus not require such additives. Generally, any conventional foaming or blowing agent, as well as lightweight filler may be utilized. Examples of specific blowing agents well known to the art, include the various known and conventional foaming or blowing agents, as well as those set forth in various texts, journals, encyclopedias, and the like, such as for example those set forth in MODERN PLASTICS ENCYCLOPEDIA, as noted above, which are hereby fully incorporated by reference. The amount of the blowing or foaming agent is simply that required in order to make the dispenser float. This is usually a very small amount and may vary from about 0.05 to about 2 parts by weight per 100 parts of polymer, with from about 0.1 to about 1.0 parts being preferred. A suitable blowing agent is Celogen. This blowing agent, as with all other desired blowing agents, degrades by release at a temperature at which the floating pesticide dispenser or composition can be extruded without degrading the components thereof. The gas creates a series of gas filled voids within the matrix. Other blowing agents include Celogen OT, Celogen RA, and the like which release nitrogen and/or carbon dioxide and/or carbon monoxide upon the application of heat thereto. Still other materials include liquids that vaporize at extrusion temperature such as dichloroethane, or carbon dioxide releasing materials such as various bicarbonates, or nitrogen releasing chemicals such as azodicarbonamide, and N,N'-dinitrosopentamethylenetetramine.

Instead of a foaming or blowing agent, a lightweight filler may be utilized. Again, such lightweight additives are known to the art and include materials such as microballoons (e.g., phenolic), powdered nut shells, powdered corn cob, wood dust, and the like. Once again, the amount required is that such that the dispenser will float. Generally, the amount may vary from about 3 to about 25 parts by weight with preferably from about 5 to about 15 parts by weight per 100 parts of polymer. Furthermore, it is noted that various thermoplastics or thermosets may also be utilized often times without any filler or blowing agent, since they often have a density of less than 1.0 grams/cm$^3$.

In order to ensure that the floating dispenser is not washed or floated away in various environments, but generally contained in a confined area, it has an anchor. The anchor should be of a weight such as to prevent it from floating away in the intended area of use. Generally, the density of the anchor is in excess of 1.5, desirably in excess of 2.7 grams per cc and the total weight is often in the range of from about 2 to about 10 or 5 to 50 times the total weight of the floating dispenser. Of course, depending upon the actual use situation, the anchor weight may be less than this range or even a specific gravity of 1.5 or 2.7 grams per cc as when utilized in an area of slow moving or stagnant water, for example, a swamp, or in excess of this weight if utilized in an area of fast moving water, for example, a brook, stream, drainage ditch, catch basin, etc.

A specific embodiment of the floating dispenser is disclosed in FIG. 1 wherein the floating dispenser is generally indicated by the numeral 10, with the anchor generally indicated by the numeral 12 which may be in the form of a weight 13. A string, line, or any other suitable connecting means 15 extends and connects the floating dispenser or chip and the anchor. The density of the anchor, as noted above, is generally in excess of 1.5 or 2.7 grams per cc and may be an item such as aluminum or steel, for example, a washer, a metal crimp, generally any other metal, or other item which serves as a suitable ballast. Desirably, the length of line 20 is such as to preclude silting over due to input of various sorts of debris, in the particular aqueous environment.

The floating herbicide dispenser, as shown in FIG. 1, thus resides within the aqueous body and can be made to reside within any depth where the undesirable aquatic plant is most susceptible to the absorption of the toxic herbicides. Moreover, depending upon the length of connecting line 15, floating herbicide dispenser 10 can be made to always float upon the water surface (not shown) regardless of typical variations in level of the water depth. This factor also affords a visible inspection.

Figure 2:
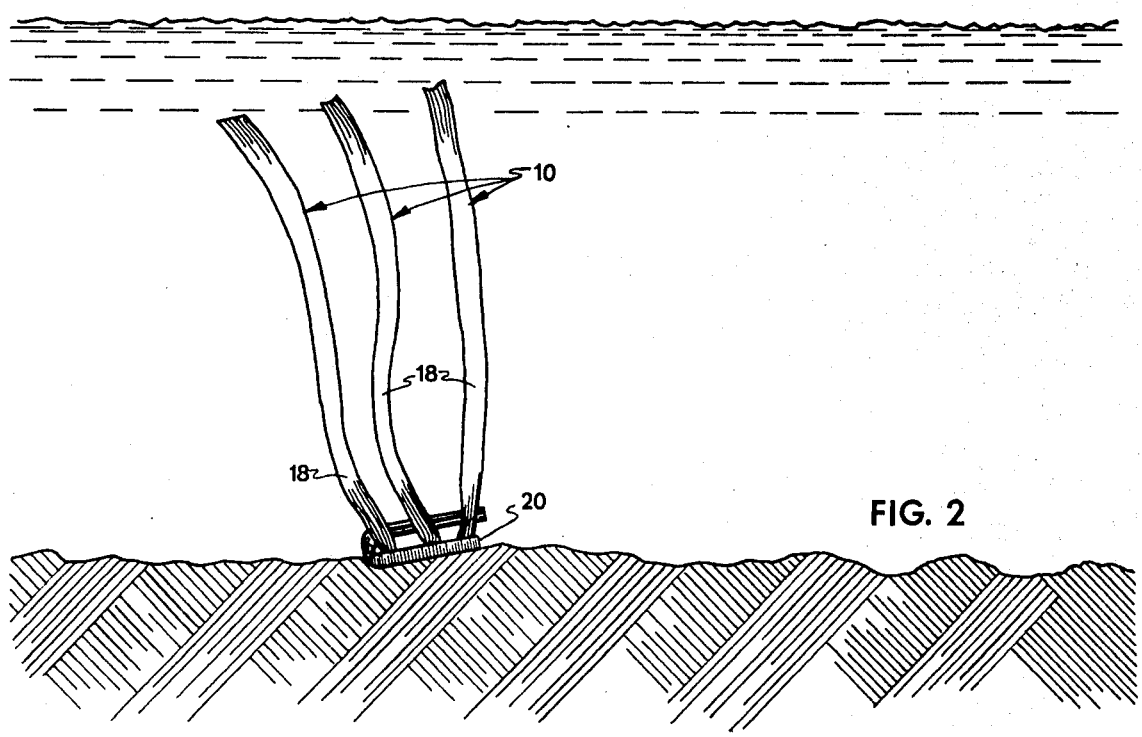
FIG. 2 is an elevational view wherein the floating herbicide dispensers are in the form of strands which are attached to a weighted anchor as in the form of a metal clamp.

A second structure for suspending a floating controlled release herbicide dispenser is in FIG. 2. In this embodiment, floating herbicide dispenser 10, which has a density of less than 1.0 grams per cc, is processed as an extruded strand, rope, or the like. One or more strands 18 are clamped together through fastener 20 which may be a metal crimp or generally any compound having a density of 1.5 or 2.7 grams or greater as well as a mass greater than that of a total number of extending strands 18. Naturally, strands 18 have a length conducive to their end use, and sufficient to avoid coverage as by slit or debris. The crimp is of suitable geometry, e.g., may have tines or legs, to prevent the strands from washing away as through flooding. Moreover, several strands may be held together as by having an enlarged bottom portion (not shown) so that a mechanical binding occurs at a fastener through which the strands cannot pass. Of course, strands may also be crimped in the center so that one length of strand becomes two strands.

Figure 3:
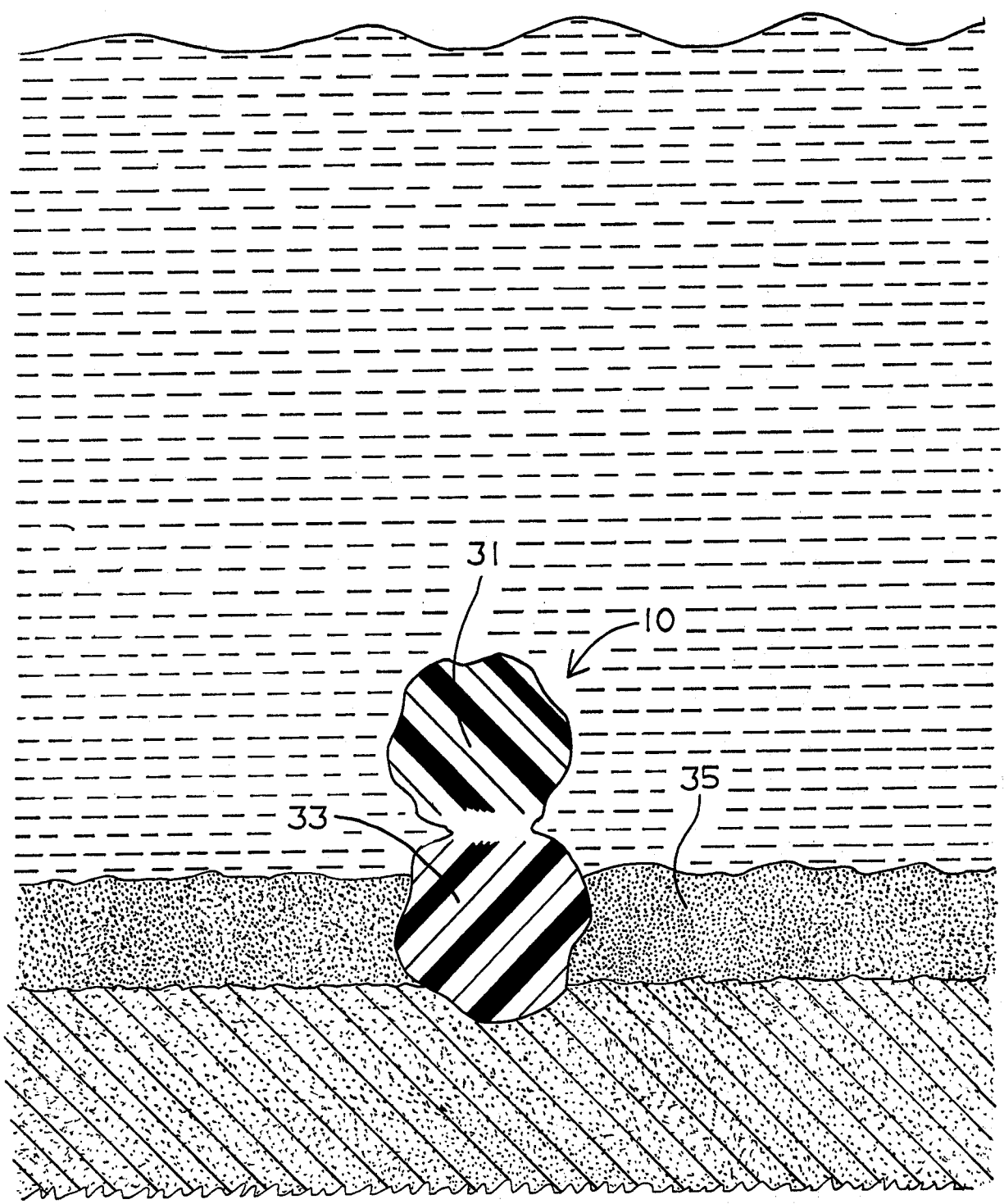
FIG. 3 is an elevational view showing a bimodal pellet having an anchor end and a floating end such that said floating end resides above the bottom of a body of water.

Another structure for a floating release dispenser is shown in FIG. 3. In this FIG., two pellets, granules, etc., are shown. Pellet 31 is a dispenser and it is attached and connected to anchor 33. In this particular drawing, the shape is that of a bimodal pellet, that is two pellets of different densities which have been connected as for example, through heating the pellets to their softening temperature and fusing them together, by melt welding or through the use of adhesives, or any other conventional manner. As apparent from FIG. 3, the bimodal pellet sits above the bottom of a body of water so that any silt, debris, a blocking layer of material, or the like, as indicated by the numeral 35 does not cover the floating portion of the bimodal pellet. The floating portion has a density of less than 1.0 grams per cc, whereas the anchor portion has a density of from about 1.02 to about 1.1 grams per cc. The net effect is that the system floats on silt, sand, mud, etc., and rises as said silt, sand, or mud depth increases with increasing deposition. Although a bimodal structure is shown in FIG. 3, multimodal pellets may exist having a plurality of floating dispenser portions as well as a plurality of anchor portions. Moreover, they may exist in various geometric forms or shapes.

As should be apparent from the above embodiments, generally any type, shape, or form of floating dispenser-anchor arrangement can be utilized within the concepts of the present invention, to effect sufficient proximity to the undesired plants. Moreover, the sizes of the various pellets, strands, anchor, and the like may vary greatly. The connection may be direct as in the bimodal pellet or it may be a connecting line of any suitable material such as a polyester, nylon, fish line, or other water-resistant material. Naturally, the floating dispenser will have incorporated therein the various components as set forth herein.

TERRESTRIAL DISPENSER METHODS

The herbicide dispensers of the present invention are utilized by applying them to soil, that is, on top of soil, and desirably by applying them within the soil. The method or manner of addition to the soil is by any conventional means such as by plowing, tilling, banding, cultivating, furrowing, and the like. Thus, the release mechanism occurs from moisture or water in the soil. Depending upon the type of undesired plant and the area of the plant most susceptible to attack, by toxins, the choice between using a low or moderate solubility porosigen or a higher solubility porosigen is determined by individual factors. Generally, since the amount of moisture in the soil is not that existing in an aquatic environment, the higher solubility porosigens are desired in the dispenser, that is, those porosigens as noted above having a solubility of from about 0.1 up to about 100 grams per 100 grams of water are preferred. As expressed above, the porosigen should be inert with regard to the thermoplastic or thermoset plastic as well as with regard to the herbicide. Moreover, it should not be harmful to the environment.

Since controlled release is dependent upon soil moisture, a hygroscopic material such as calcium chloride which attracts moisture can be utilized as a matrix additive for use in dryer soils. The range of the hygroscopic material is from about one half to about 25 and preferably from about 1 to 5 parts by weight per 100 parts of polymer. Other examples of specific hygroscopic compounds include $P_2O_5$, $Mg(ClO_4)_2$, KOH, $Al_2O_3$, and $Ba(ClO_4)_2$.

Different herbicides will release at different rates, dependent upon water solubility, partition coefficient, cohesive energy density, molecular size, and other physical and chemical properties of the agent molecule and the matrix. Moreover, different amounts of the compound can be varied as well as the amount of porosigen to give a desirable release rate, such that the undesired plant, is generally controlled; that is, eliminated, killed, kept in check, or the like. Examples for terrestrial and aquatic use follow.

EXAMPLES

For a variety of undesired aquatic plant types, the following table illustrates aquatic weeds good for study.

TABLE 2

| COMMON NAME* | BIOLOGICAL NAME | TYPE |
|---|---|---|
| Elodea (E) | Elodea canadensis | submerged, floating may root, usually not |
| Vallisneria (V) | Vallisneria americana | rooted bottom, grass |
| Cabomba (C) | Cabomba caroliniana | submerged, floating |
| Eurasian Watermilfoil (M) | Myriaphyllum spicatum | submerged, floating usually does not root |
| Water hyacinth | Eichornia crassipes | surface floating weed |
| Southern Naiad | Najas guadalupensis | submerged, floating |
| Alligator weed | Alternanthera philoxeroides | reed |
| Water lettuce | Pistia stratiotes | surface floating weed |
| Duckweed (D) | Lemna minor | surface floating weed |

*parenthetical symbols to be used in bioassay data below.

In preparation of the aquatic weed studies, the following polymer compounds were available for mixing according to the preferred production methods for the thermoplastic polymers, as seen in Table 3.

TABLE 3

| POLYMER | Matrix Elements TYPE | SOURCE |
|---|---|---|
| LDPE (low density polyethylene) | Chemplex 1023B | Chemplex |
| | MN718 | U.S. Industrial Chemical |
| | MN710 | U.S. Industrial Chemical |
| | MN703 | U.S. Industrial Chemical |
| HDPE (high density polyethylene) | Chemplex 6001 | Chemplex |
| EVA (ethylvinyl acetate) copolymer | Chemplex 3315 | Chemplex |
| PP (polypropylene) | P-460 | Hanotech |
| PS (polystyrene) | P-400 | Hanotech |
| Polyester | Hytril | DuPont |
| Polyamide | Elvamide 6001 | DuPont |
| Polyvinyl acetate | Ayac 5710 | Union Carbide |
| Urethane | Estone 5701 F1 | B.F. Goodrich |
| Ethylene-propylene copolymer | Vistalon 702 | Exxon Chemical Co. |

In order to fully illustrate the nature of the invention, a number of examples are provided. Recipes are given along with bioassay data. Data has been accumulated in regard to aquatic weeds.

The formulations used consisted of the herbicide agent incorporated into a polymer matrix or a polymer alloy, i.e., wherein two polymers of divergent melt indices are uniformly mixed in the molten state so as to adjust free volume as described above. Various porosigens are likewise incorporated in the matrix in such a manner as to evaluate said porosigen alone or in combination thereof. A higher solubility or "fast" porosigen such as ammonium sulfate, and optionally with a porosity constituent such as ethylene glycol, normally provides a rapid herbicide emission. A low or moderate solubility or "slow" porosigen such as calcium carbonate, and optionally with a porosity constituent such as silicon dioxide, normally provides the slow development of a pore network and thus slow herbicide emission. By combining a "fast" and a "slow" porosigen and respective porosity constituents, release characteristics are suitably altered so that a desired rate may be obtained. The ability to tailor the given compound to a given or desired herbicide emission rate is especially important for use in a terrestrial soil environment wherein said soils vary in moisture content and the physiochemical properties that govern the transport and absorption of xenobiotics such as herbicides.

EXAMPLE 1—DIURON COMPOUNDS

The following Table 4 lists the several recipes for controlled release diuron formulations.

TABLE 4

DIURON RECIPES
INGREDIENT (Weight Percent)

| CODE | MN 718 | VISTALON 702 | ZINC STEARATE | DIURON | CaCO$_3$ | (NH$_4$)SO$_4$ | SiO$_2$ | ETHYLENE GLYCOL |
|---|---|---|---|---|---|---|---|---|
| 1A | 29.0 | 29.0 | 1 | 31.0 | — | 10 | — | — |
| 1B | 29.0 | 29.0 | 1 | 31.0 | 5 | 5 | — | — |
| 1C | 29.0 | 29.0 | 1 | 31.0 | 5 | — | 5 | — |
| 1D | 28.0 | 28.0 | 1 | 21.0 | 10 | — | — | 2 |
| 1E | 28.0 | 28.0 | 1 | 31.0 | 5 | 5 | — | 2 |
| 1F | 24.5 | 24.5 | 1 | 31.0 | 5 | 6 | 4 | 4 |
| 1G | 24.5 | 24.5 | 1 | 31.0 | 10 | 4 | 5 | — |
| 1H | 24.0 | 24.0 | 1 | 31.0 | 10 | 10 | — | — |

The Diuron compounds from the above table were bioassayed against select aquatic weeds and select terrestrial weeds. The aquatic bioassays were performed by adding a measured pellet dosage of 10 ppm and 1 ppm to 1 gallon aquaria, said aquaria containing 1 gallon of demineralized water and three test plants potted in soil. Each evaluation, i.e., each formulation at each dosage was replicated five times against each aquatic plant. Plants were in part laboratory grown using techniques common to the art and outdoor grown (mil foil). Plants were examined daily for mortality.

Average mortality was computed by averaging the mortality of each group of replicates. Results for the plants in Table 2 are provided in the following Table 5.

TABLE 5

Diuron Bioassay: Aquatic Plants

| | DOSAGE | | Plant Mortality (accum. %) by day number | | | | | | | |
|---|---|---|---|---|---|---|---|---|---|---|
| CODE | (ppm) | PLANT | 5 | 10 | 15 | 20 | 25 | 30 | 40 | 50 |
| 1A | 1 | E | 3 | 5 | 21 | 45 | 65 | 88 | 100 | — |
| 1A | 10 | E | 0 | 5 | 18 | 27 | 55 | 57 | 80 | 90 |
| 1A | 1 | V | 0 | 0 | 2 | 5 | 10 | 18 | 50 | 60 |
| 1A | 10 | V | 0 | 0 | 2 | 7 | 20 | 40 | 83 | 97 |
| 1A | 1 | C | 3 | 5 | 26 | 43 | 60 | 77 | 100 | — |
| 1A | 10 | C | 3 | 15 | 85 | 95 | 97 | 100 | — | — |

TABLE 5-continued

Diuron Bioassay: Aquatic Plants

| CODE | DOSAGE (ppm) | PLANT | Plant Mortality (accum. %) by day number | | | | | | | |
|------|--------------|-------|----|----|----|----|----|----|----|----|
|      |              |       | 5  | 10 | 15 | 20 | 25 | 30 | 40 | 50 |
| 1A | 1  | M | 5  | 5  | 17 | 23 | —  | —  | —  | —  |
| 1A | 10 | M | 17 | 27 | 57 | 90 | 100| —  | —  | —  |
| 1B | 1  | E | 0  | 0  | 3  | 13 | 27 | 30 | 100| —  |
| 1B | 10 | E | 7  | 27 | 73 | 80 | 83 | 86 | 100| —  |
| 1B | 1  | V | 5  | 10 | 15 | 23 | 30 | 42 | 63 | 76 |
| 1B | 10 | V | 5  | 5  | 11 | 17 | 37 | 55 | 87 | 94 |
| 1B | 1  | C | 5  | 15 | 22 | 25 | 50 | 94 | 100| —  |
| 1B | 10 | C | 3  | 15 | 71 | 100| —  | —  | —  | —  |
| 1B | 1  | M | 5  | 10 | 20 | 35 | —  | —  | —  | —  |
| 1B | 10 | M | 17 | 27 | 43 | 93 | —  | —  | —  | —  |
| 1C | 1  | E | 0  | 0  | 0  | 3  | 3  | 7  | 50 | 60 |
| 1C | 10 | E | 3  | 7  | 23 | 37 | 47 | 75 | 95 | 99 |
| 1C | 1  | V | 0  | 3  | 7  | 17 | 25 | 34 | 67 | 75 |
| 1C | 10 | V | 7  | 10 | 23 | 35 | 50 | 64 | 85 | 90 |
| 1C | 1  | C | 0  | 3  | 15 | 22 | 35 | 60 | 100| —  |
| 1C | 10 | C | 0  | 0  | 40 | 93 | 100| —  | —  | —  |
| 1C | 1  | M | 3  | 5  | 7  | 60 | —  | —  | —  | —  |
| 1C | 10 | M | 17 | 40 | 67 | 93 | 100| —  | —  | —  |
| 1D | 1  | E | 0  | 0  | 15 | 15 | 17 | 32 | 77 | 95 |
| 1D | 10 | E | 3  | 7  | 51 | 65 | 80 | 100| —  | —  |
| 1D | 1  | V | 0  | 5  | 19 | 27 | 35 | 55 | 77 | 90 |
| 1D | 10 | V | 7  | 13 | 27 | 40 | 65 | 65 | 85 | 96 |
| 1D | 1  | C | 3  | 20 | 50 | 50 | 53 | 88 | 97 | 100|
| 1D | 10 | C | 17 | 60 | 100| —  | —  | —  | —  | —  |
| 1D | 1  | M | 0  | 0  | 0  | 10 | —  | —  | —  | —  |
| 1D | 10 | M | 13 | 17 | 27 | 90 | —  | —  | —  | —  |
| 1E | 1  | E | 0  | 0  | 5  | 17 | 27 | 49 | 95 | 95 |
| 1E | 10 | E | 0  | 5  | 13 | 25 | 45 | 67 | 100| —  |
| 1E | 1  | V | 0  | 0  | 2  | 3  | 3  | 8  | 80 | 87 |
| 1E | 10 | V | 3  | 5  | 10 | 10 | 27 | 36 | 60 | 70 |
| 1E | 1  | C | 5  | 17 | 32 | 43 | 95 | 100| —  | —  |
| 1E | 10 | C | 0  | 27 | 81 | 93 | 95 | 100| —  | —  |
| 1E | 1  | M | 0  | 3  | 10 | 13 | —  | —  | —  | —  |
| 1E | 10 | M | 25 | 43 | 85 | 100| —  | —  | —  | —  |
| 1F | 1  | E | 3  | 5  | 34 | 43 | 55 | 76 | 93 | 97 |
| 1F | 10 | E | 0  | 7  | 42 | 53 | 75 | 98 | 100| —  |
| 1F | 1  | V | 0  | 3  | 10 | 15 | 17 | 28 | 83 | 90 |
| 1F | 10 | V | 0  | 3  | 28 | 50 | 65 | 65 | 80 | 90 |
| 1F | 1  | C | 0  | 5  | 22 | 30 | 37 | 75 | 100| —  |
| 1F | 10 | C | 5  | 35 | 85 | 100| —  | —  | —  | —  |
| 1F | 1  | M | 5  | 15 | 17 | 37 | —  | —  | —  | —  |
| 1F | 10 | M | 17 | 45 | 73 | 100| —  | —  | —  | —  |
| 1G | 1  | E | 3  | 13 | 37 | 47 | 65 | 84 | 95 | 95 |
| 1G | 10 | E | 5  | 17 | 54 | 67 | 77 | 80 | 95 | 95 |
| 1G | 1  | V | 0  | 0  | 5  | 7  | 13 | 20 | 73 | 75 |
| 1G | 10 | V | 5  | 5  | 25 | 47 | 63 | 70 | 75 | 85 |
| 1G | 1  | C | 5  | 10 | 23 | 33 | 47 | 88 | 100| —  |
| 1G | 10 | C | 0  | 13 | 60 | 80 | 100| —  | —  | —  |
| 1G | 1  | M | 0  | 7  | 7  | 20 | —  | —  | —  | —  |
| 1G | 10 | M | 53 | 77 | 87 | 97 | 100| —  | —  | —  |
| 1H | 1  | E | 3  | 13 | 20 | 35 | 35 | 54 | 70 | 90 |
| 1H | 10 | E | 10 | 23 | 45 | 60 | 85 | 100| —  | —  |
| 1H | 1  | V | 0  | 0  | 2  | 3  | 0  | 0  | 13 | 17 |
| 1H | 10 | V | 3  | 3  | 5  | 10 | 15 | 22 | 75 | 83 |
| 1H | 1  | C | 0  | 5  | 16 | 33 | 63 | 85 | 100| —  |
| 1H | 10 | C | 0  | 3  | 53 | 97 | 100| —  | —  | —  |
| 1H | 1  | M | 0  | 0  | 0  | 5  | —  | —  | —  | —  |
| 1H | 10 | M | 10 | 23 | 27 | 27 | —  | —  | —  | —  |

Examination of the Diruon data indicates that release rate is a porperty of the porosigen utilized. As can be seen, formulation 1A utilizing the "fast" porosigen, 10 percent ammonium sulfate, shows the most rapid plant destruction. When the total porosigen content is kept at 10 percent but now altered to consist of 5 percent $(NH_4)_2SO_4$ and 5 percent $CaCO_3$, a "slow" porosigen, the loss rate, as measured by bioassay, decreases (formulation 1B). Now mixing $CaCO_3$ and ethylene glycol (formulation D), the latter being a pososity activating constituent, the loss rate shows a slight decrease. Using a "slow" porosigen and a "slow" porosity modifying constituent (formulation 1C), a further decrease in loss rate, as measured by bioassay, is seen. Varying the $CaCO_3$ and $(NH_4)_2SO_4$ ratio, as in formulation 1G, compared to formulation 1B, also varies the loss rate.

Diuron compounds have been evaluated against terrestrial weeds common to a farm plot in Northeastern Ohio. Pelletized material was broadcast on plowed test sites at rates normal to agricultural usage. Periodic measurements were made evaluating total weed content and dandelion content, in the latter case the weed being planted by broadcasting of seed, whereas in the former weeds being voluntary, comprising mainly ragweed, golden rod, barnyard grasses, buckhorn, dandelion and various other unidentified dicots and monocots. Results are indicated in the following tables.

TABLE 6

| CODE | DOSAGE | Total Weed Content/Square Foot by Days 15 | 26 | 34 | 44 | AVERAGE WEED HEIGHT AFTER 44 DAYS |
|---|---|---|---|---|---|---|
| 1D | 5#/acre | 19.4 | 8.0 | 7.2 | 13.2 | 4 inch |
| 1D | 20#/acre | 11.8 | 3.4 | 3.0 | 2.4 | 3 inch |
| Control | 0 | 39 | 30 | 34 | 50+ | 13 inch |
| 1F | 5#/acre | 10.2 | 9.4 | 8.6 | 10.4 | 4 inch |
| 1F | 20#/acre | 10.0 | 2.2 | 0.8 | 2.8 | 2 inch |
| Control | 0 | 46 | 24.4 | 52 | 50+ | 12 inch |
| 1H | 5#/acre | 11.6 | 8.8 | 8.4 | 11.2 | 6 inch |
| 1H | 20#/acre | 10.2 | 6.4 | 7.8 | 14.2 | 5 inch |
| Control | 0 | 29 | 19.8 | 21.4 | 50+ | 13 inch |

TABLE 7

DANDELION CONTENT/100 SQUARE FEET

| CODE | DOSAGE | 26 days | 34 days | 44 days |
|---|---|---|---|---|
| 1D | 5#/acre | 0 | 2 | 2 |
| 1D | 20#/acre | 0 | 5 | 9 |
| Control | 0 | 15 | 14 | * |
| 1F | 5#/acre | 0 | 1 | 16 |
| 1F | 20#/acre | 0 | 0 | 2 |
| Control | 0 | 12 | 20 | * |
| 1H | 5#/acre | 6 | 6 | 0 |
| 1H | 20#/acre | 6 | 9 | 0 |
| Control | 0 | 14 | 13 | * |

*Dandelion shaded out by other broadleaf weeds.

It is readily apparent that weed population and weed height is greatly controlled by the controlled release compositions shown above.

EXAMPLE 2

Controlled release formulations having 2,4-D acid, as shown in the following table were examined against various aquatic weeds using the techniques described under Example 1. Bioassay data is repeated below.

TABLE 8

2,4-D ACID RECIPES
Ingredients (Weight Percent)

| CODE | % HERBICIDE | VISTALON 702 | MN-718 | ZnSt | CaCO₃ | SiO₂ | As | EG |
|---|---|---|---|---|---|---|---|---|
| 2A | 25 | 74 | — | 1 | — | — | — | — |
| 2B | 25 | — | 74 | 1 | — | — | — | — |
| 2C | 25 | 32 | 32 | 1 | — | — | 10 | — |
| 2D | 25 | 32 | 32 | 1 | 5 | — | 5 | — |
| 2E | 25 | 32 | 32 | 1 | 5 | 5 | — | — |
| 2F | 25 | 31 | 31 | 1 | 10 | — | — | 2 |
| 2G | 25 | 31 | 31 | 1 | 5 | — | 5 | 2 |
| 2H | 25 | 27.5 | 27.5 | 1 | 5 | 4 | 6 | 4 |
| 2I | 25 | 27.5 | 27.5 | 1 | 10 | 5 | 4 | — |
| 2J | 25 | 27 | 27 | 1 | 10 | — | 10 | — |

TABLE 9

2,4-D ACID BIOASSAY: AQUATIC PLANTS

| CODE | DOSAGE (ppm) | PLANT | 4 | 10 | 15 | 20 | 25 | 30 | 35 | 42 |
|---|---|---|---|---|---|---|---|---|---|---|
| 2A | 1 | E | 0 | 0 | 5 | 7 | 5 | 5 | 10 | 10 |
| 2A | 10 | E | 0 | 0 | 0 | 0 | 0 | 0 | 0 | 0 |
| 2A | 1 | M | 0 | 10 | 13 | 15 | 0 | 0 | 0 | 0 |
| 2A | 10 | M | 0 | 45 | 57 | 57 | 0 | 0 | 0 | 0 |
| 2B | 1 | E | 0 | 0 | 0 | 0 | 0 | 0 | 5 | 5 |
| 2B | 10 | E | 0 | 5 | 5 | 5 | 0 | 0 | 0 | 0 |
| 2B | 1 | V | 3 | 3 | 3 | 3 | 0 | 0 | 3 | 10 |
| 2B | 10 | V | 13 | 10 | 10 | 10 | 7 | 7 | 20 | 30 |
| 2C | 1 | V | 25 | 37 | 45 | 65 | 75 | 75 | 75 | 80 |
| 2C | 10 | V | 15 | 17 | 17 | 33 | 40 | 60 | 63 | 73 |
| 2C | 1 | C | 0 | 13 | 17 | 60 | 63 | 65 | 75 | 77 |
| 2C | 10 | C | 0 | 13 | 17 | 30 | 70 | 77 | 83 | 83 |
| 2C | 1 | M | 15 | 37 | 53 | 73 | 0 | 0 | 0 | 0 |
| 2C | 10 | M | 20 | 55 | 63 | 77 | 0 | 0 | 0 | 0 |
| 2D | 1 | V | 33 | 33 | 45 | 50 | 63 | 63 | 63 | 63 |
| 2D | 10 | V | 20 | 13 | 25 | 37 | 53 | 63 | 73 | 85 |
| 2D | 1 | C | 0 | 7 | 7 | 10 | 10 | 13 | 20 | 40 |
| 2D | 10 | C | 5 | 5 | 13 | 17 | 50 | 53 | 57 | 60 |
| 2D | 1 | M | 3 | 15 | 23 | 25 | 0 | 0 | 0 | 0 |
| 2D | 10 | M | 35 | 67 | 70 | 77 | 0 | 0 | 0 | 0 |
| 2E | 1 | C | 5 | 7 | 13 | 25 | 40 | 45 | 47 | 47 |
| 2G | 10 | C | 10 | 23 | 45 | 100 | 0 | 0 | 0 | 0 |
| 2E | 1 | E | 7 | 7 | 7 | 7 | 5 | 5 | 5 | 5 |
| 2E | 10 | E | 3 | 5 | 5 | 5 | 7 | 7 | 7 | 7 |
| 2E | 1 | V | 20 | 30 | 40 | 50 | 53 | 63 | 70 | 70 |
| 2E | 10 | V | 27 | 30 | 33 | 47 | 50 | 60 | 77 | 83 |
| 2E | 1 | C | 0 | 0 | 3 | 20 | 53 | 53 | 53 | 53 |
| 2E | 10 | C | 0 | 7 | 13 | 27 | 57 | 57 | 60 | 73 |
| 2E | 1 | M | 5 | 23 | 33 | 63 | 0 | 0 | 0 | 0 |
| 2E | 10 | M | 7 | 17 | 20 | 30 | 0 | 0 | 0 | 0 |
| 2F | 1 | E | 0 | 0 | 0 | 0 | 0 | 0 | 0 | 0 |
| 2F | 10 | E | 7 | 15 | 45 | 70 | 70 | 70 | 70 | 70 |
| 2F | 1 | V | 10 | 13 | 15 | 15 | 3 | 3 | 3 | 3 |
| 2F | 10 | V | 15 | 35 | 50 | 75 | 77 | 80 | 80 | 80 |
| 2F | 1 | C | 3 | 3 | 10 | 43 | 87 | 93 | 95 | 97 |
| 2F | 10 | C | 3 | 5 | 5 | 10 | 50 | 50 | 55 | 90 |
| 2F | 1 | M | 0 | 15 | 23 | 33 | 0 | 0 | 0 | 0 |
| 2F | 10 | M | 10 | 55 | 60 | 75 | 0 | 0 | 0 | 0 |
| 2G | 1 | E | 0 | 3 | 3 | 3 | 3 | 5 | 7 | 7 |
| 2G | 10 | E | 3 | 53 | 70 | 100 | 0 | 0 | 0 | 0 |
| 2G | 1 | V | 7 | 5 | 10 | 10 | 7 | 17 | 50 | 53 |
| 2G | 10 | V | 13 | 25 | 27 | 40 | 37 | 45 | 50 | 53 |
| 2G | 1 | C | 5 | 7 | 13 | 25 | 40 | 45 | 47 | 47 |

TABLE 9-continued 2,4-D ACID BIOASSAY: AQUATIC PLANTS

| CODE | DOSAGE (ppm) | PLANT | Mortality (Accumulative Percent) By Day | | | | | | | |
|---|---|---|---|---|---|---|---|---|---|---|
| | | | 4 | 10 | 15 | 20 | 25 | 30 | 35 | 42 |
| 2G | 10 | C | 10 | 23 | 45 | 100 | 0 | 0 | 0 | 0 |
| 2H | 1 | E | 0 | 3 | 5 | 10 | 20 | 20 | 20 | 20 |
| 2H | 10 | E | 3 | 10 | 25 | 45 | 50 | 50 | 43 | 47 |
| 2H | 1 | V | 3 | 17 | 13 | 27 | 47 | 50 | 60 | 65 |
| 2H | 10 | V | 13 | 17 | 25 | 33 | 77 | 80 | 80 | 80 |
| 2H | 1 | C | 7 | 5 | 17 | 25 | 35 | 40 | 40 | 40 |
| 2H | 10 | C | 15 | 20 | 33 | 67 | 80 | 85 | 97 | 100 |
| 2H | 1 | M | 0 | 30 | 45 | 63 | 0 | 0 | 0 | 0 |
| 2H | 10 | M | 5 | 37 | 45 | 67 | 0 | 0 | 0 | 0 |
| 2I | 1 | E | 0 | 0 | 0 | 7 | 10 | 10 | 7 | 7 |
| 2I | 10 | E | 7 | 7 | 10 | 15 | 20 | 20 | 20 | 17 |
| 2I | 1 | V | 10 | 15 | 23 | 27 | 5 | 5 | 13 | 15 |
| 2I | 10 | V | 10 | 10 | 10 | 10 | 10 | 0 | 0 | 0 |
| 2I | 1 | C | 0 | 0 | 0 | 7 | 25 | 30 | 40 | 40 |
| 2I | 10 | C | 5 | 25 | 30 | 43 | 43 | 47 | 53 | 53 |
| 2I | 1 | M | 10 | 33 | 40 | 45 | 0 | 0 | 0 | 0 |
| 2I | 10 | M | 25 | 43 | 63 | 70 | 0 | 0 | 0 | 0 |
| 2J | 1 | E | 0 | 3 | 3 | 7 | 0 | 0 | 0 | 0 |
| 2J | 10 | E | 3 | 43 | 60 | 85 | 77 | 77 | 85 | 90 |
| 2J | 1 | V | 10 | 5 | 10 | 15 | 15 | 17 | 17 | 20 |
| 2J | 10 | V | 3 | 15 | 25 | 30 | 55 | 40 | 40 | 35 |
| 2J | 1 | C | 5 | 7 | 13 | 33 | 37 | 45 | 45 | 45 |
| 2J | 10 | C | 7 | 20 | 60 | 90 | 100 | 0 | 0 | 0 |
| 2J | 1 | M | 10 | 15 | 15 | 20 | 0 | 0 | 0 | 0 |
| 2J | 10 | M | 15 | 47 | 67 | 73 | 0 | 0 | 0 | 0 |

Analysis of the bioassay data indicates that where no porosigen is present, formulations 2A and 2B, plant kill is minimal (due solely to wash off at the herbicide molecules on or near the dispenser surface), in turn indicating very low or no release of said herbicide. Again, data evaluation shows that compound 2C containing a fast porosigen offers substantially faster plant destruction than compound 2D additionally containing a slow porosigen. Compound 2F, additionally containing ethylene glycol, a porosity activator, is significantly faster in herbicidal action compared to compound 2E having a slow porosigen and a comparable porosity modifying constituent.

2,4-D acid compounds were also evaluated against terrestrial weeds in the fashion described under Example 1. Results are shown in the following table.

TABLE 10

| | DOSAGE | Total Weed Content/Square Foot By Days | | | Average Weed Height |
|---|---|---|---|---|---|
| CODE | (ppm) | 26 | 34 | 44 | After 44 days |
| 2F | 2#/acre | 7.2 | 15.8 | 23.2 | 7 inch |
| 2F | 10#/acre | 21.2 | 6.8 | 12.2 | 6 inch |
| Control | 0 | 18.6 | 14.6 | 50+ | 13 inch |
| 2H | 2#/acre | 2.0 | 12.8 | 21.2 | 7 inch |
| 2H | 10#/acre | 17.6 | 8.4 | 4.2 | 6 inch |
| Control | 0 | 014.8 | 10.0 | 50+ | 10 inch |
| 2J | 2#/acre | 5.4 | 9.6 | 18.0 | 6 inch |
| 2J | 10#/acre | 12.4 | 9.8 | 12.8 | 5 inch |
| Control | 0 | 14.2 | 7.0 | 5.0 | 10 inch |

TABLE 11

| Dandelion Content/100 Square Feet | | | | |
|---|---|---|---|---|
| CODE | DOSAGE | 26 days | 34 days | 44 days |
| 2F | 2#/acre | 14 | 30 | 50 |
| 2F | 10#/acre | 11 | 20 | 43 |
| Control | 0 | 16 | 32 | * |
| 2H | 2#/acre | 6 | 10 | 16 |
| 2H | 10#/acre | 1 | 3 | 25 |
| Control | 0 | 14 | 17 | * |
| 2J | 2#/acre | 14 | 23 | 32 |
| 2J | 10#/acre | 9 | 9 | 20 |

TABLE 11-continued

| Dandelion Content/100 Square Feet | | | | |
|---|---|---|---|---|
| CODE | DOSAGE | 26 days | 34 days | 44 days |
| Control | 0 | 13 | 30 | * |

Again, the tables above readily indicate the improvements of undesirable plant control shown by the controlled release compositions.

EXAMPLE 3

Diquat, a well recognized aquatic herbicide was similarly evaluated against select aquatic weeds. Unlike the other herbicidal agents evaluated, Diquat is highly water soluble and thus exhibits both the properties of a porosigen as well as the properties of a herbicide. The following tables depict the formulations examined and bioassay data.

TABLE 12

| DIQUAT RECIPES PERCENT INGREDIENTS | | | | | | | | |
|---|---|---|---|---|---|---|---|---|
| CODE | % HERBICIDE | VISTALON 702 | MN-718 | ZnSt | $CaCO_3$ | $SiO_2$ | As | EG |
| 3A | 25 | 74 | — | 1 | — | — | — | — |
| 3B | 25 | — | 74 | 1 | — | — | — | — |
| 3C | 25 | 32 | 32 | 1 | — | — | 10 | — |
| 3D | 25 | 32 | 32 | 1 | 5 | — | 5 | — |
| 3E | 25 | 32 | 32 | 1 | 5 | 5 | — | — |
| 3F | 25 | 31 | 31 | 1 | 10 | — | — | 2 |
| 3G | 25 | 31 | 31 | 1 | 5 | — | 5 | 2 |
| 3H | 25 | 27.5 | 27.5 | 1 | 5 | 4 | 6 | 4 |
| 3I | 25 | 27.5 | 27.5 | 1 | 10 | 5 | 4 | — |
| 3J | 25 | 27 | 27 | 1 | 10 | — | 10 | — |

TABLE 13

DIQUAT BIOASSAYS: AQUATIC PLANTS

| CODE | DOSAGE (ppm) | PLANT | Mortality (accumulative %) By Day 4 | 10 | 15 | 20 | 25 | 30 |
|---|---|---|---|---|---|---|---|---|
| 3A | 1 | E | 30 | 90 | 100 | — | — | — |
| 3A | 10 | E | 25 | 85 | 100 | — | — | — |
| 3A | 1 | V | 3 | 27 | 73 | 97 | 100 | — |
| 3A | 10 | V | 0 | 43 | 97 | 100 | — | — |
| 3A | 1 | C | 0 | 25 | 35 | 40 | 60 | 100 |
| 3A | 10 | C | 0 | 15 | 25 | 35 | 60 | 100 |
| 3A | 1 | M | 50 | 65 | 67 | 73 | — | — |
| 3A | 10 | M | 73 | 77 | 83 | 85 | — | — |
| 3B | 1 | E | 5 | 83 | 93 | 100 | — | — |
| 3B | 10 | E | 45 | 95 | 100 | — | — | — |
| 3B | 1 | V | 5 | 63 | 75 | 100 | — | — |
| 3B | 10 | V | 10 | 70 | 97 | 100 | — | — |
| 3B | 1 | C | 0 | 10 | 10 | 17 | 25 | — |
| 3B | 10 | C | 0 | 17 | 43 | 80 | 100 | — |
| 3B | 1 | M | 30 | 35 | 37 | 45 | — | — |
| 3B | 10 | M | 63 | 77 | 75 | 75 | — | — |
| 3C | 1 | E | 23 | 93 | 100 | — | — | — |
| 3C | 10 | E | 25 | 100 | — | — | — | — |
| 3C | 1 | V | 3 | 7 | 25 | 63 | 95 | 100 |
| 3C | 10 | V | 0 | 20 | 77 | 97 | 100 | — |
| 3C | 1 | C | 0 | 7 | 20 | 25 | 35 | — |
| 3C | 10 | C | 3 | 7 | 27 | 50 | 70 | — |
| 3C | 1 | M | 30 | 47 | 75 | 93 | — | — |
| 3C | 10 | M | 67 | 73 | 83 | 87 | — | — |
| 3D | 1 | E | 13 | 63 | 75 | 100 | — | — |
| 3D | 10 | E | 13 | 75 | 95 | 100 | — | — |
| 3D | 1 | V | 3 | 7 | 25 | 63 | 95 | 100 |
| 3D | 10 | V | 0 | 20 | 77 | 97 | 100 | — |
| 3D | 1 | C | 0 | 13 | 25 | 33 | 37 | — |
| 3D | 10 | C | 7 | 35 | 50 | 80 | 97 | — |
| 3D | 1 | M | 33 | 60 | 65 | 75 | — | — |
| 3D | 10 | M | 57 | 85 | 90 | 93 | — | — |
| 3E | 1 | E | 13 | 80 | 100 | — | — | — |
| 3E | 10 | E | 20 | 77 | 100 | — | — | — |
| 3E | 1 | V | 3 | 30 | 73 | 100 | — | — |
| 3E | 10 | V | 0 | 75 | 97 | 100 | — | — |
| 3E | 1 | C | 0 | 17 | 45 | 65 | 73 | — |
| 3E | 10 | C | 0 | 20 | 47 | 80 | 97 | — |
| 3E | 1 | M | 5 | 20 | 37 | 77 | — | — |
| 3E | 10 | M | 65 | 75 | 80 | 80 | — | — |
| 3F | 1 | E | 15 | 85 | 100 | — | — | — |
| 3F | 10 | E | 17 | 85 | 100 | — | — | — |
| 3F | 1 | V | 0 | 37 | 83 | 100 | — | — |
| 3F | 10 | V | 0 | 80 | 100 | — | — | — |
| 3F | 1 | C | 10 | 50 | 77 | 93 | 100 | — |
| 3F | 10 | C | 3 | 35 | 75 | 100 | — | — |
| 3F | 1 | M | 57 | 65 | 75 | 100 | — | — |
| 3F | 10 | M | 83 | 87 | 87 | 93 | — | — |
| 3G | 1 | E | 0 | 67 | 100 | — | — | — |
| 3G | 10 | E | 3 | 87 | 100 | — | — | — |
| 3G | 1 | V | 3 | 20 | 70 | 97 | 100 | — |
| 3G | 10 | V | 10 | 55 | 100 | — | — | — |
| 3G | 1 | C | 0 | 5 | 40 | 47 | 60 | — |
| 3G | 10 | C | 10 | 50 | 75 | 95 | 100 | — |
| 3G | 1 | M | 37 | 57 | 83 | 97 | 100 | — |
| 3G | 10 | M | 55 | 73 | 83 | 97 | 100 | — |
| 3H | 1 | E | 45 | 93 | 100 | — | — | — |
| 3H | 10 | E | 53 | 93 | 100 | — | — | — |
| 3H | 1 | V | 5 | 47 | 80 | 100 | — | — |
| 3H | 10 | V | 5 | 45 | 93 | 100 | — | — |
| 3H | 1 | C | 0 | 30 | 83 | 100 | — | — |
| 3H | 10 | C | 10 | 80 | 100 | — | — | — |
| 3H | 1 | M | — | 35 | 83 | 93 | 100 | — |
| 3H | 10 | M | — | 80 | 87 | 93 | 97 | 100 |
| 3I | 1 | E | 20 | 97 | 100 | — | — | — |
| 3I | 10 | E | 45 | 95 | 100 | — | — | — |
| 3I | 1 | V | 0 | 20 | 50 | 80 | 100 | — |
| 3I | 10 | V | 3 | 47 | 83 | 100 | — | — |
| 3I | 1 | C | 30 | 37 | 63 | 80 | 90 | — |
| 3I | 10 | C | 3 | 47 | 85 | 97 | 100 | — |
| 3I | 1 | M | 43 | 85 | 100 | — | — | — |
| 3I | 10 | M | 77 | 97 | 97 | 97 | 100 | — |
| 3J | 1 | E | 5 | 100 | — | — | — | — |
| 3J | 10 | E | 10 | 100 | — | — | — | — |
| 3J | 1 | V | 0 | 10 | 63 | 83 | 100 | — |
| 3J | 10 | V | 5 | 27 | 67 | 95 | 100 | — |
| 3J | 1 | C | 0 | 25 | 47 | 57 | 70 | — |
| 3J | 10 | C | 10 | 60 | 87 | 93 | 100 | — |
| 3J | 1 | M | 33 | 50 | 80 | 97 | 100 | — |
| 3J | 10 | M | 67 | 83 | 90 | 100 | — | — |

Due to the highly water soluble nature of Diquat, it is readily emitted without benefit of porosigen. Thus, the porosigen free formulation 3A and 3B kill rapidly. In turn, this rapid loss is not favorable because the emission life is greatly retarded. In contrast to all other materials, the presence of a porosigen slows herbicide emission. Thus, the controlled emission rate is obtained. 3C containing ammonium sulfate, a fast porosigen, acts at a slower rate against the various plants; than the porosigen free material. The loss rate observed is still slower for compound 3E with a lower water solubility porosigen and porosity modifying constituent.

EXAMPLE 4

In a similar fashion, Atrazine compounds were prepared in accordance with the recipes of the following table. Said compounds were evaluated against aquatic plants using techniques described under Example 1. Results of said evaluation are presented below.

TABLE 14

ATRAZINE - RECIPES

Ingredients (weight percent)

| CODE | % HERBICIDE | VISTALON 702 | MN-718 | ZnSt | CaCO$_3$ | SiO$_2$ | As | EG |
|---|---|---|---|---|---|---|---|---|
| 4A | 31.30 | — | 67.7 | 1 | — | — | — | — |
| 4B | 31 | 29 | 29 | 1 | — | — | 10 | — |
| 4C | 31 | 29 | 29 | 1 | 5 | — | 5 | — |
| 4D | 31 | 29 | 29 | 1 | 5 | 5 | — | — |
| 4E | 31 | 28 | 28 | 1 | 10 | — | — | 2 |
| 4F | 31 | 28 | 28 | 1 | 5 | — | 5 | 2 |
| 4G | 31 | 24.5 | 24.5 | 1 | 5 | 4 | 6 | 4 |
| 4H | 31 | 24.5 | 24.5 | 1 | 10 | 5 | 4 | — |
| 4I | 31 | 24.5 | 24 | 1 | 10 | — | 10 | — |

TABLE 15

ATRAZINE BIOASSAYS: AQUATIC PLANTS

| CODE | DOSAGE (ppm) | PLANT | Mortality (accumulative %) By Day 4 | 10 | 15 | 20 | 25 | 30 | 35 | 42 |
|---|---|---|---|---|---|---|---|---|---|---|
| 4A | 1 | E | 0 | 0 | 0 | 0 | 0 | 0 | 0 | 0 |
| 4A | 10 | E | 0 | 0 | 0 | 7 | 7 | 10 | 17 | 20 |
| 4B | 1 | V | 3 | 7 | 7 | 7 | 0 | 10 | 25 | 37 |
| 4B | 10 | V | 20 | 27 | 33 | 55 | 75 | 80 | 87 | 100 |
| 4B | 1 | C | 5 | 5 | 20 | 45 | 75 | 75 | 75 | 87 |
| 4B | 10 | C | 7 | 7 | 7 | 37 | 63 | 65 | 77 | 100 |
| 4C | 1 | V | 15 | 23 | 45 | 65 | 67 | 73 | 73 | 85 |
| 4C | 10 | V | 33 | 40 | 40 | 40 | 30 | 63 | 80 | 85 |
| 4C | 1 | C | 5 | 10 | 20 | 73 | 90 | 93 | 95 | 100 |
| 4C | 10 | C | 0 | 10 | 25 | 55 | 75 | 75 | 75 | 97 |
| 4D | 1 | E | 0 | 0 | 0 | 13 | 10 | 10 | 10 | 5 |
| 4D | 10 | E | 3 | 3 | 3 | 5 | 3 | 17 | 30 | 35 |
| 4D | 1 | V | 7 | 13 | 13 | 17 | 3 | 3 | 17 | 60 |
| 4D | 10 | V | 7 | 13 | 27 | 45 | 73 | 75 | 90 | 100 |
| 4D | 1 | C | 3 | 5 | 33 | 75 | 93 | 90 | 97 | 100 |
| 4D | 10 | C | 10 | 25 | 50 | 73 | 87 | 90 | 95 | 100 |
| 4E | 1 | C | 0 | 0 | 0 | 0 | 7 | 37 | 57 | 73 |
| 4E | 10 | C | 0 | 0 | 0 | 0 | 10 | 37 | 45 | 75 |
| 4F | 1 | V | 10 | 10 | 23 | 40 | 30 | 45 | 57 | 73 |
| 4F | 10 | V | 13 | 17 | 23 | 30 | 37 | 50 | 55 | 60 |
| 4F | 1 | C | 0 | 0 | 0 | 3 | 0 | 0 | 17 | 60 |

TABLE 15-continued

ATRAZINE BIOASSAYS: AQUATIC PLANTS

| CODE | DOS-AGE (ppm) | PLANT | Mortality (accumulative %) By Day | | | | | | | |
|---|---|---|---|---|---|---|---|---|---|---|
| | | | 4 | 10 | 15 | 20 | 25 | 30 | 35 | 42 |
| 4F | 10 | C | 0 | 0 | 0 | 3 | 0 | 17 | 30 | 70 |
| 4G | 1 | V | 0 | 0 | 0 | 3 | 10 | 13 | 15 | 15 |
| 4G | 10 | V | 0 | 5 | 15 | 27 | 47 | 53 | 65 | 73 |
| 4G | 1 | C | 0 | 3 | 5 | 13 | 20 | 23 | 33 | 50 |
| 4G | 10 | C | 0 | 0 | 0 | 0 | 3 | 20 | 30 | 70 |
| 4H | 1 | E | 0 | 3 | 3 | 3 | 37 | 40 | 40 | 40 |
| 4H | 10 | V | 0 | 0 | 0 | 3 | 10 | 10 | 15 | 27 |
| 4H | 1 | C | 10 | 10 | 15 | 15 | 33 | 47 | 73 | 90 |
| 4H | 10 | C | 3 | 3 | 3 | 3 | 57 | 63 | 70 | 70 |
| 4I | 1 | C | 0 | 0 | 0 | 0 | 43 | 43 | 47 | 55 |
| 4I | 10 | C | 3 | 7 | 10 | 20 | 30 | 55 | 57 | 60 |

Results indicate that release of the herbicide occurs; and again those formulations containing a fast porosigen, e.g., 4B, release at a more efficacious rate than those with no porosigen, 4A, or a slow porosigen, for example 4G and 4I.

EXAMPLE 5

Fenac Compounds

Fenac formulations were prepared in accordance with the following recipes and bioassayed against Elodea and Milfoil. Test methods were as described in Example 1.

TABLE 16

| CODE | FENAC | M-718 | EPM | ZINC STEARATE | CaCO₃ | SiO₂ | (NH₄)₂SO₄ | ETHYLENE GLYCOL |
|---|---|---|---|---|---|---|---|---|
| 5A | 5 | — | 94 | 1 | — | — | — | — |
| 5B | 5 | 94 | — | 1 | — | — | — | — |
| 5C | 5 | 42 | 42 | 1 | — | — | 10 | — |
| 5D | 5 | 42 | 42 | 1 | 5 | — | 5 | — |
| 5E | 5 | 42 | 42 | 1 | 5 | 5 | — | — |
| 5F | 5 | 41 | 41 | 1 | 10 | — | — | 2 |
| 5G | 5 | 41 | 41 | 1 | 5 | — | 5 | 2 |
| 5H | 5 | 37.5 | 37.5 | 1 | 5 | 4 | 6 | 4 |
| 5I | 5 | 37.5 | 37.5 | 1 | 10 | 5 | 4 | — |
| 5J | 5 | 37.5 | 37.5 | 1 | 10 | — | 10 | — |

LT₅₀ (lethal time to 50 percent plant mortality) values are given in the next table.

TABLE 17

Fenac Compounds: Bioassay with *Elodea Canadensis* and Eurasian Watermilfoil (*Myriophyllum Spicatum*) 37-Day Evaluation

| CODE | DOSAGE (ppm) | LT₅₀ | |
|---|---|---|---|
| | | ELODEA | WATERMILFOIL |
| 5A | 1 | not achieved* | not achieved* |
| 5B | 1 | not achieved* | not achieved* |
| | 10 | not achieved* | not achieved* |
| 5C | 1 | 28 days | 18 days |
| | 10 | 18 days | 13 days |
| 5D | 1 | 33 days | not achieved* |
| | 10 | 24 days | 14 days |
| 5E | 1 | 34 days | 35 days |
| | 10 | 34 days | 33 days |
| 5F | 1 | 34 days | 32 days |

TABLE 17-continued

Fenac Compounds: Bioassay with *Elodea Canadensis* and Eurasian Watermilfoil (*Myriophyllum Spicatum*) 37-Day Evaluation

| CODE | DOSAGE (ppm) | LT₅₀ | |
|---|---|---|---|
| | | ELODEA | WATERMILFOIL |
| | 10 | 28 days | 18 days |
| 5G | 1 | 35 days | 29 days |
| | 10 | 29 days | 8 days |
| 5H | 1 | not achieved* | not achieved* |
| | 10 | 27 days | 11 days |
| 5I | 1 | 37 days | 21 days |
| | 10 | 29 days | 16 days |
| 5J | 1 | not achieved* | 25 days |
| | 10 | 28 days | 7 days |

*release is too slow for effective plant destruction

Again, examination of the data indicates that compounds 5A and 5B, having no porosigen content are ineffectual whereas compounds 5C and 5G, having a fast porosigen present show rapid kill, and compounds 5E, containing a slow porosigen, shows a slow destruction of the test plant.

EXAMPLE 6

Similarly, controlled release composition recipes containing Dichlobenil are given below.

TABLE 18

Dichlobenil Recipes

Ingredients (Weight Percent)

| CODE | % HERBICIDE (50% W.P.) | VISTALON 702 | MN-718 LDPE | ZnSt | CaCO₃ | SiO₂ | AS | EG |
|---|---|---|---|---|---|---|---|---|
| 6D | 10 | 33.5 | 33.5 | 1 | 10 | — | — | 2 |
| 6F | 10 | 30 | 30 | 1 | 5 | 4 | 6 | 4 |
| 6H | 10 | 29.5 | 29.5 | 1 | 10 | — | 10 | — |

Dichlobenil releasing formulations were evaluated against terrestrial weeds with the results shown below.

TABLE 19

| COMPOUND | CONCENTRATION | Weeds/Square Foot at Day No. | | | | AVERAGE WEED HEIGHT - DAY 44 |
|---|---|---|---|---|---|---|
| | | 15 | 26 | 34 | 44 | |
| 6D | 4#/acre | 30.0 | 10.8 | 20.6 | 13 | 6 inches |
| 6D | 12#/acre | 3.8 | 2.6 | 3.6 | 5.2 | 4 inches |
| Control | 0 | 23.8 | 12.0 | 41.6 | 50+ | 15 inches |
| 6F | 4#/acre | 8.2 | 9.2 | 9.4 | 8.0 | 5 inches |
| 6F | 12#/acre | 4.8 | 2.4 | 2.8 | 2.0 | 4 inches |
| Control | 0 | 8.4 | 9.0 | 17.4 | 50+ | 16 inches |
| 6H | 4#/acre | 9.8 | 8.8 | 5.2 | 5.2 | 5 inches |
| 6H | 12#/acre | 2.0 | 2.2 | 0.8 | 2.0 | 3 inches |
| Control | 0 | 15.4 | 16.8 | 43 | 50+ | 13 inches |

TABLE 20

| COMPOUND | CONCENTRATION | Dandelions/100 Square Foot at Day No. | | |
|---|---|---|---|---|
| | | 26 | 34 | 44 |
| 6D | 4#/acre | 0 | 0 | 2 |
| 6D | 12#/acre | 1 | 1 | 0 |
| Control | 0 | 11 | 8 | * |
| 6F | 4#/acre | 1 | 1 | 12 |
| 6F | 12#/acre | 1 | 1 | 2 |
| Control | 0 | 15 | 14 | * |
| 6H | 4#/acre | 1 | 1 | 0 |
| 6H | 12#/acre | 3 | 3 | 0 |
| Control | 0 | 30 | 8 | * |

*dandelion obscured by ragweed and other weeds

EXAMPLE 7

Various Bromacil recipes were prepared in accordance with the following recipes. These were evaluated against several aquatic plants using the method described under Example 1.

TABLE 21
BROMACIL RECIPES

| CODE | % HERBICIDE | VISTALON 702 | MN-718 | ZnSt | CaCO$_3$ | SiO$_2$ | As | EG |
|---|---|---|---|---|---|---|---|---|
| 7A | 31 | 29 | 29 | 1 | — | — | 10 | — |
| 7B | 31 | 29 | 29 | 1 | 5 | — | 5 | — |
| 7C | 31 | 29 | 29 | 1 | 5 | 5 | — | — |
| 7D | 31 | 28 | 28 | 1 | 10 | — | — | 2 |
| 7E | 31 | 28 | 28 | 1 | 5 | — | 5 | 2 |
| 7F | 31 | 24.5 | 24.5 | 1 | 5 | 4 | 6 | 4 |
| 7G | 31 | 24.5 | 24.5 | 1 | 10 | 5 | 4 | — |
| 7H | 31 | 24 | 24 | 1 | 10 | — | 10 | — |

TABLE 22
Bromacil Bioassay Results (35-day Test Period)

| CODE | DOSAGE (ppm) | PLANT | LT$_{50}$(days) |
|---|---|---|---|
| 7A | 1 | E | 35 days |
| | 10 | E | 31 days |
| | 1 | M | 35+ days* |
| | 10 | M | 15 |
| 7B | 1 | E | 15 days |
| | 10 | E | 27 days |
| 7C | 1 | E | 35+ days* |
| | 10 | E | 30 days |
| | 10 | M | 19 days |
| 7D | 1 | E | 35+ days* |
| | 10 | E | 30 days |
| | 1 | M | 23 days |
| | 10 | M | 17 days |
| 7E | 1 | E | 27 days |
| | 10 | E | 18 days |
| | 10 | M | 8 days |
| 7F | 1 | E | 35 days |
| | 10 | E | 26 days |
| | 10 | M | 10 days |
| 7G | 1 | E | 35+ days* |
| | 10 | E | 35+ days* |
| | 1 | M | 21 days |
| | 10 | M | 21 days |
| 7H | 1 | E | 34 days |
| | 1 | M | 30 days |
| | 10 | M | 15 days |

*indicates that the LT$_{50}$ is over 35 days

Undesirable plant destriction is achieved, as seen above.

EXAMPLE 8

Fenac was incorporated in a polymer alloy in accordance with the recipes shown below.

TABLE 23

| INGREDIENT (Code 8A) | Percent By Weight |
|---|---|
| LDPE (MN-718) | 24 |
| EVA (MU-763) | 24 |
| Zinc Stearate | 1 |
| CaCO$_3$ | 24 |
| Fenac | 24 |

Bioassay was performed against several aquatic weeds with the LT$_{50}$ values shown below.

TABLE 24

| CODE | PELLET DOSAGE (ppm) | LT$_{50}$ (by days) | | |
|---|---|---|---|---|
| | | E | C | D |
| 8A | 2 | * | * | 23 |
| | 5 | 21 | * | 24 |
| | 10 | 15 | 22 | * |

*Test not performed

While in accordance with the patent statutes a base mode for carrying out the invention has been provided, the invention is not be limited thereby or thereto. Therefore, for an understanding of the scope of the invention, reference is had to the following claims.

What is claimed is:

1. A controlled release herbicide dispenser, comprising:
   (a) from about 10 parts to about 160 parts by weight of a herbicide;
   (b) from about 15 parts to about 80 parts by weight of an inert porosigen, said porosigen having a solubility of from about 0.0005 to about 100 grams per 100 grams of water; and
   (c) about 100 parts of a polymer selected from the group consisting of thermoplastic polymers, thermoset polymers, and combinations thereof;
   said herbicide and said porosigen distributed throughout said polymer to form a controlled release herbicide dispenser so that upon contact with moisture or water, said porosigen is dissolved gradually to create a pore structure within the dispenser and, said herbicide is released at a controlled rate to retard and eliminate growth of undesired plants.

2. A controlled release herbicide dispenser, according to claim 1, wherein said porosigen has a concentration of from about 1 part to about 40 parts by weight; and wherein said porosigen is selected from the group consisting of the salts, hydrates, and oxides of alkaline metals, alkaline earth metals, nickel, tin, and silver; and ammonium bromide, ammonium carbonate, ammonium bicarbonate, ammonium chlorate, ammonium chloride, ammonium fluoride, ammonium sulfate, sodium carbonate, and sodium bicarbonate.

3. A controlled release herbicide dispenser, according to claim 1, wherein said porosigen is selected from the group consisting of an oxide and a salt, said oxide and salt having a cation selected from the group consisting of the alkaline metals, the alkaline earth metals, iron, zinc, nickel, silver and tin, and said salt having an anion selected from the group consisting of a carbonate, bicarbonate, nitrate, nitrite, nitride, peroxide, phosphate, phosphite, phosphide, sulfate, sulfite, sulfide and said porosigen having a solubility of from about 0.0005 to about 0.01 grams per 100 grams of water.

4. A controlled release herbicide dispenser, according to claim 3, wherein said porosigen is selected from the group consisting of carbonates of magnesium, calcium, and strontium cations, and combinations thereof.

5. A controlled release herbicide dispenser, according to claim 1, wherein moisture or said water removes said porosigen and creates a pore structure in the dispenser.

6. A process for the controlled release of a herbicide from a dispenser, comprising:
    (a) adding and mixing 100 parts by weight of a polymer, from about 10 parts to about 160 parts by weight of a herbicide, and from about 15 parts to about 80 parts by weight by an inert porosigen, said porosigen having a solubility of from about 0.0005 to about 100 grams per 100 grams of water;
    (b) forming a matrix from said polymer within which said porosigen and said herbicide are dispersed; and
    (c) applying and contacting said matrix with the environment so that upon contact with moisture or water, said porosigen is dissolved gradually to create a pore structure within the dispenser and, said herbicide will be released to retard and eliminate undesired plant growth.

7. A method for the controlled release of herbicides into an environment, comprising:
    (a) dispersing a matrix into the environment, said matrix comprising a polymer, a herbicide, and a porosigen, said porosigen being soluble in water and being present in an amount of between 15 parts and about 80 parts porosigen per 100 parts polymer, by weight;
    (b) dissolving said porosigen from said matrix at a controlled rate upon contact with water, to create a pore structure in said matrix;
    (c) dislodging said herbicide through said pore structure from said matrix upon contact with water, said herbicide to retard and eliminate growth of undesired plants; and
    said porosigen having a water solubility less than 100 grams per 100 grams of water and said polymer being water insoluble and non-porous.

8. A method for the controlled release of herbicides into an environment, according to claim 7, wherein said dispersing comprises contacting said matrix with the terrestrial environment.

9. A composition for destroying pestiferous plants, comprising:
    a mixture of a herbicidally effective active ingredient which is water dispersible and an inert particulate material having a water solubility of less than 100 grams per 100 grams of water at 25° C., said herbicidal ingredient being of the dimethylamine salts of 2,4-dichlorophenoxyacetic acid, said inert particulate material being calcium carbonate;
    said mixture being dispersed within a water insoluble, non-porous polymeric material, said polymeric material being a copolymer of ethylene-vinyl acetate;
    the proportion of particulate material being between 15 parts and 80 parts per 100 parts polymer by weight and sufficient to create a pore structure within said matrix and expose the herbicidal ingredient within said matrix upon exposure of the matrix to water.

10. A controlled release herbicide dispenser, comprising:
    (a) from about 10 parts to about 160 parts by weight of a herbicide, said herbicide being of the dimethylamine salts of 2,4-dichlorophenoxyacetic acid;
    (b) from about 15 parts to about 80 parts by weight of a porosigen, said porosigen being calcium carbonate;
    (c) about 100 parts of a polymer selected from the group consisting of a thermoplastic polymer, said thermoplastic polymer being a copolymer of ethylene-vinyl acetate;
    said polymer in said matrix containing said herbicide and said porosigen to effect a controlled release of said herbicide, upon contact with water, to retard and eliminate growth of undesired plants.

* * * * *

UNITED STATES PATENT AND TRADEMARK OFFICE
CERTIFICATE OF CORRECTION

PATENT NO. : 4,405,360
DATED : September 20, 1983
INVENTOR(S) : Nathan F. Cardarelli It is certified that error appears in the above-identified patent and that said Letters Patent are hereby corrected as shown below:

Cover Page, In the title, delete "THERMOPLASTIC" and substitute therefor --PLASTIC--.
Column 1, In the Title, delete "THERMOPLASTIC" and substitute therefor --PLASTIC--.
Column 2, Line 66, delete "and" and substitute therefor --are--.
Column 12, Line 35, delete "of" and substitute therefor --and--.
Column 14, Line 1, delete "3,6dichloro-0-anisic" and substitute therefor --3,6-dichloro-0-anisic--.
Column 18, Line 43, delete "temperature" and insert therefor --temperatures--.

Signed and Sealed this

Fourteenth Day of February 1984

[SEAL]

Attest:

GERALD J. MOSSINGHOFF

Attesting Officer

Commissioner of Patents and Trademarks